US008688234B2

(12) United States Patent
Zhu et al.

(10) Patent No.: US 8,688,234 B2
(45) Date of Patent: Apr. 1, 2014

(54) DEVICES, METHODS, AND SYSTEMS INCLUDING CARDIAC PACING

(75) Inventors: Qingsheng Zhu, Wexford, PA (US); Daniel Felipe Ortega, Buenos Aires (AR); Julio Cesar Spinelli, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 69 days.

(21) Appl. No.: 13/139,951

(22) PCT Filed: Dec. 18, 2009

(86) PCT No.: PCT/US2009/068859
§ 371 (c)(1),
(2), (4) Date: Jan. 6, 2012

(87) PCT Pub. No.: WO2010/071849
PCT Pub. Date: Jun. 24, 2010

(65) Prior Publication Data
US 2012/0101539 A1    Apr. 26, 2012

Related U.S. Application Data

(60) Provisional application No. 61/139,094, filed on Dec. 19, 2008, provisional application No. 61/139,109, filed on Dec. 19, 2008, provisional application No. 61/139,117, filed on Dec. 19, 2008, provisional application No. 61/139,126, filed on Dec. 19, 2008, provisional application No. 61/139,197, filed on Dec. 19, 2008, provisional application No. 61/139,211, filed on Dec. 19, 2008, provisional application No. 61/139,181, filed on Dec. 19, 2008, provisional application No. 61/139,220, filed on Dec. 19, 2008, provisional application No. 61/139,226, filed on Dec. 19, 2008, provisional application No. 61/139,236, filed on Dec. 19, 2008, provisional application No. 61/139,249, filed on Dec. 19, 2008.

(51) Int. Cl.
*A61N 1/00* (2006.01)

(52) U.S. Cl.
USPC .................................. 607/119; 607/4

(58) Field of Classification Search
USPC ........................................ 607/4, 119
See application file for complete search history.

(56) References Cited

U.S. PATENT DOCUMENTS 3,614,955 A    10/1971   Mirowski
3,804,098 A     4/1974   Friedman
(Continued)

FOREIGN PATENT DOCUMENTS

AU    2005319498 B2    7/2011
DE       2827595 A1    4/1979
(Continued)

OTHER PUBLICATIONS

"U.S. Appl. No. 10/004,695, Non-Final Office Action mailed Dec. 22, 2003", 6 pgs.
(Continued)

*Primary Examiner* — Nicole F Lavert
(74) *Attorney, Agent, or Firm* — Schwegman Lundberg & Woessner, P.A.

(57) ABSTRACT

A pacing output circuit can be configured to generate a ventricular pacing signal configured to be delivered to an electrode near the His bundle in a right ventricle of a heart to pace the right and left ventricles and improve synchronization of at least one of the ventricles relative to intrinsic activity. In an example, the ventricular pacing signal can include first and second signal components in opposite polarity from each other with respect to a reference component, the first and second signal components having substantially identical duration and magnitude.

18 Claims, 11 Drawing Sheets

(56) References Cited

U.S. PATENT DOCUMENTS

| | | |
|---|---|---|
| 3,866,615 A | 2/1975 | Hewson |
| 3,911,928 A | 10/1975 | Lagergren |
| 3,942,536 A | 3/1976 | Mirowski et al. |
| 3,949,757 A | 4/1976 | Sabel |
| 3,995,623 A | 12/1976 | Blake et al. |
| 4,026,303 A | 5/1977 | Babotai |
| 4,030,508 A | 6/1977 | Thalen |
| 4,057,067 A | 11/1977 | Lajos |
| 4,106,512 A | 8/1978 | Bisping |
| 4,136,703 A | 1/1979 | Wittkampf |
| 4,154,247 A | 5/1979 | O'Neill |
| 4,217,913 A | 8/1980 | Dutcher |
| 4,258,725 A | 3/1981 | O'Neill |
| 4,278,093 A | 7/1981 | Lafortune et al. |
| 4,282,885 A | 8/1981 | Bisping |
| 4,289,134 A | 9/1981 | Bernstein |
| 4,289,144 A | 9/1981 | Gilman |
| 4,311,153 A | 1/1982 | Smits |
| 4,332,259 A | 6/1982 | McCorkle, Jr. |
| 4,365,639 A | 12/1982 | Goldreyer |
| 4,393,883 A | 7/1983 | Smyth et al. |
| 4,402,329 A | 9/1983 | Williams |
| 4,437,474 A | 3/1984 | Peers-Trevarton |
| 4,458,677 A | 7/1984 | McCorkle, Jr. |
| 4,458,695 A | 7/1984 | Peers-Trevarton |
| 4,463,765 A | 8/1984 | Gold |
| 4,469,104 A | 9/1984 | Peers-Trevarton |
| 4,497,326 A | 2/1985 | Curry |
| 4,540,236 A | 9/1985 | Peers-Trevarton |
| 4,543,956 A | 10/1985 | Herscovici |
| 4,549,548 A | 10/1985 | Wittkampf et al. |
| 4,559,951 A | 12/1985 | Dahl et al. |
| 4,567,901 A | 2/1986 | Harris |
| 4,570,642 A | 2/1986 | Kane et al. |
| 4,577,643 A | 3/1986 | Beranek |
| 4,589,420 A | 5/1986 | Adams et al. |
| 4,602,645 A | 7/1986 | Barrington et al. |
| 4,603,705 A | 8/1986 | Speicher et al. |
| 4,624,265 A | 11/1986 | Grassi |
| 4,624,266 A | 11/1986 | Kane |
| 4,627,439 A | 12/1986 | Harris |
| 4,630,204 A | 12/1986 | Mortara |
| 4,633,880 A | 1/1987 | Osypka et al. |
| 4,641,649 A | 2/1987 | Walinsky et al. |
| 4,643,201 A | 2/1987 | Stokes |
| 4,646,755 A | 3/1987 | Kane |
| 4,649,937 A | 3/1987 | DeHaan et al. |
| 4,649,938 A | 3/1987 | McArthur |
| 4,664,113 A | 5/1987 | Frisbie et al. |
| 4,667,686 A | 5/1987 | Peers-Trevarton |
| H356 H | 11/1987 | Stokes et al. |
| 4,721,115 A | 1/1988 | Owens |
| 4,751,931 A | 6/1988 | Briller et al. |
| 4,784,161 A | 11/1988 | Skalsky et al. |
| 4,785,815 A | 11/1988 | Cohen |
| 4,799,486 A | 1/1989 | DuFault |
| 4,799,493 A | 1/1989 | DuFault |
| 4,819,647 A | 4/1989 | Byers et al. |
| 4,819,661 A | 4/1989 | Heil, Jr. et al. |
| 4,819,662 A | 4/1989 | Heil, Jr. et al. |
| 4,876,109 A | 10/1989 | Mayer et al. |
| 4,886,074 A | 12/1989 | Bisping |
| 4,892,102 A | 1/1990 | Astrinsky |
| 4,895,152 A | 1/1990 | Callaghan et al. |
| 4,922,607 A | 5/1990 | Doan et al. |
| 4,922,927 A | 5/1990 | Fine et al. |
| 4,924,881 A | 5/1990 | Brewer |
| 4,953,564 A | 9/1990 | Berthelsen |
| 4,967,766 A | 11/1990 | Bradshaw |
| 4,972,848 A | 11/1990 | DiDomenico et al. |
| 4,994,078 A | 2/1991 | Jarvik |
| 5,002,067 A | 3/1991 | Berthelsen et al. |
| 5,007,864 A | 4/1991 | Stutz, Jr. |
| 5,016,646 A | 5/1991 | Gotthardt et al. |
| 5,036,848 A | 8/1991 | Hewson |
| 5,050,001 A | 9/1991 | Kupersmith et al. |
| 5,056,516 A | 10/1991 | Spehr |
| 5,063,932 A | 11/1991 | Dahl et al. |
| 5,076,285 A | 12/1991 | Hess et al. |
| 5,083,564 A | 1/1992 | Scherlag |
| 5,092,879 A | 3/1992 | Jarvik |
| 5,129,404 A | 7/1992 | Spehr et al. |
| 5,144,960 A | 9/1992 | Mehra et al. |
| 5,152,299 A | 10/1992 | Soukup |
| 5,174,289 A | 12/1992 | Cohen |
| 5,179,962 A | 1/1993 | Dutcher et al. |
| 5,181,511 A | 1/1993 | Nickolls et al. |
| 5,223,226 A | 6/1993 | Wittmar et al. |
| 5,242,430 A | 9/1993 | Arenas et al. |
| 5,255,693 A | 10/1993 | Dutcher et al. |
| 5,259,394 A | 11/1993 | Bens |
| 5,259,395 A | 11/1993 | Li |
| 5,267,560 A | 12/1993 | Cohen |
| 5,275,620 A | 1/1994 | Darby et al. |
| 5,282,845 A | 2/1994 | Bush et al. |
| 5,299,569 A | 4/1994 | Wernicke et al. |
| 5,300,108 A | 4/1994 | Rebell et al. |
| 5,304,219 A | 4/1994 | Chernoff et al. |
| 5,306,292 A | 4/1994 | Lindegren |
| 5,313,953 A | 5/1994 | Yomtov et al. |
| 5,320,642 A | 6/1994 | Scherlag |
| 5,324,327 A | 6/1994 | Cohen |
| 5,336,252 A | 8/1994 | Cohen |
| 5,342,414 A | 8/1994 | Mehra |
| 5,344,439 A | 9/1994 | Otten |
| 5,358,516 A | 10/1994 | Myers et al. |
| 5,366,496 A | 11/1994 | Dahl et al. |
| 5,370,665 A | 12/1994 | Hudrlik |
| 5,374,286 A | 12/1994 | Morris |
| 5,381,790 A | 1/1995 | Kanesaka |
| 5,393,929 A | 2/1995 | Yagihashi |
| 5,405,373 A | 4/1995 | Petersson et al. |
| 5,411,544 A | 5/1995 | Mar et al. |
| 5,425,755 A | 6/1995 | Doan |
| 5,433,735 A | 7/1995 | Zanakis et al. |
| 5,439,391 A | 8/1995 | McEtchin et al. |
| 5,447,533 A | 9/1995 | Vachon et al. |
| 5,447,534 A | 9/1995 | Jammet |
| 5,456,706 A | 10/1995 | Pless et al. |
| 5,456,708 A | 10/1995 | Doan et al. |
| 5,466,253 A | 11/1995 | Doan |
| 5,476,497 A | 12/1995 | Mower et al. |
| 5,476,499 A | 12/1995 | Hirschberg |
| 5,476,501 A | 12/1995 | Stewart et al. |
| 5,476,502 A | 12/1995 | Rubin |
| 5,492,119 A | 2/1996 | Abrams |
| 5,500,008 A | 3/1996 | Fain |
| 5,514,172 A | 5/1996 | Mueller |
| 5,515,848 A | 5/1996 | Corbett, III et al. |
| 5,522,874 A | 6/1996 | Gates |
| 5,524,338 A | 6/1996 | Martynuik et al. |
| 5,527,344 A | 6/1996 | Arzbaecher et al. |
| 5,531,780 A | 7/1996 | Vachon |
| 5,545,201 A | 8/1996 | Helland et al. |
| 5,554,178 A | 9/1996 | Dahl et al. |
| 5,571,163 A | 11/1996 | Helland |
| 5,578,068 A | 11/1996 | Laske et al. |
| 5,593,405 A | 1/1997 | Osypka |
| 5,593,433 A | 1/1997 | Spehr et al. |
| 5,609,158 A | 3/1997 | Chan |
| 5,628,778 A | 5/1997 | Kruse et al. |
| 5,628,779 A | 5/1997 | Bornzin et al. |
| 5,634,829 A | 6/1997 | Kerul |
| 5,634,899 A | 6/1997 | Shapland et al. |
| 5,674,272 A | 10/1997 | Bush et al. |
| 5,674,274 A | 10/1997 | Morgan et al. |
| 5,683,447 A | 11/1997 | Bush et al. |
| 5,702,427 A | 12/1997 | Ecker et al. |
| 5,709,753 A | 1/1998 | Olson et al. |
| 5,716,390 A | 2/1998 | Li |
| 5,718,720 A | 2/1998 | Prutchi et al. |
| 5,720,099 A | 2/1998 | Parker et al. |
| 5,728,140 A | 3/1998 | Salo et al. |
| 5,733,323 A | 3/1998 | Buck et al. |

(56) References Cited

U.S. PATENT DOCUMENTS

| | | |
|---|---|---|
| 5,755,766 A | 5/1998 | Chastain et al. |
| 5,769,881 A | 6/1998 | Schroeppel et al. |
| 5,772,693 A | 6/1998 | Brownlee |
| 5,782,898 A | 7/1998 | Dahl et al. |
| 5,800,464 A | 9/1998 | Kieval |
| 5,800,465 A | 9/1998 | Thompson et al. |
| 5,807,306 A | 9/1998 | Shapland et al. |
| 5,810,887 A | 9/1998 | Accorti, Jr. et al. |
| 5,814,077 A | 9/1998 | Sholder et al. |
| 5,814,079 A | 9/1998 | Kieval |
| 5,851,227 A | 12/1998 | Spehr |
| 5,861,013 A | 1/1999 | Peck et al. |
| 5,871,506 A | 2/1999 | Mower |
| 5,871,529 A | 2/1999 | Bartig et al. |
| 5,871,531 A | 2/1999 | Struble |
| 5,876,399 A | 3/1999 | Chia et al. |
| 5,876,431 A | 3/1999 | Spehr et al. |
| 5,916,214 A | 6/1999 | Cosio et al. |
| 5,925,045 A | 7/1999 | Reimels et al. |
| 5,935,159 A | 8/1999 | Cross, Jr. et al. |
| 5,941,868 A | 8/1999 | Kaplan |
| 5,944,710 A | 8/1999 | Dev et al. |
| 5,964,795 A | 10/1999 | McVenes et al. |
| 5,972,416 A | 10/1999 | Reimels et al. |
| 5,995,871 A | 11/1999 | Knisley |
| 6,006,139 A | 12/1999 | Kruse et al. |
| 6,007,476 A | 12/1999 | Wascher et al. |
| 6,024,739 A | 2/2000 | Ponzi et al. |
| 6,059,726 A | 5/2000 | Lee et al. |
| 6,070,104 A | 5/2000 | Hine et al. |
| 6,086,582 A | 7/2000 | Altman et al. |
| 6,096,069 A | 8/2000 | Bischoff |
| 6,123,084 A | 9/2000 | Jandak et al. |
| 6,141,588 A | 10/2000 | Cox et al. |
| 6,141,594 A | 10/2000 | Flynn et al. |
| 6,144,879 A * | 11/2000 | Gray .................... 607/20 |
| 6,161,029 A | 12/2000 | Spreigl et al. |
| 6,165,164 A | 12/2000 | Hill et al. |
| 6,212,434 B1 | 4/2001 | Scheiner et al. |
| 6,219,581 B1 | 4/2001 | Schaldach et al. |
| 6,230,061 B1 | 5/2001 | Hartung |
| 6,236,887 B1 | 5/2001 | Ben-Haim et al. |
| 6,254,573 B1 | 7/2001 | Haim et al. |
| 6,256,541 B1 | 7/2001 | Heil et al. |
| 6,267,778 B1 | 7/2001 | Cohen |
| 6,309,370 B1 | 10/2001 | Haim et al. |
| 6,341,235 B1 | 1/2002 | Mower |
| 6,345,204 B1 | 2/2002 | Scheiner et al. |
| 6,358,247 B1 | 3/2002 | Altman et al. |
| 6,363,286 B1 | 3/2002 | Zhu et al. |
| 6,416,510 B1 | 7/2002 | Altman et al. |
| 6,463,334 B1 | 10/2002 | Flynn et al. |
| 6,468,263 B1 | 10/2002 | Fischell et al. |
| 6,471,697 B1 | 10/2002 | Lesh |
| 6,484,057 B2 | 11/2002 | Ideker et al. |
| 6,505,082 B1 | 1/2003 | Scheiner et al. |
| 6,535,766 B1 | 3/2003 | Thompson et al. |
| 6,540,725 B1 | 4/2003 | Ponzi |
| 6,542,775 B2 | 4/2003 | Ding et al. |
| 6,544,270 B1 | 4/2003 | Zhang |
| 6,547,787 B1 | 4/2003 | Altman et al. |
| 6,556,874 B2 | 4/2003 | Audoglio |
| 6,560,489 B2 | 5/2003 | Hauck |
| 6,575,931 B1 | 6/2003 | Ponzi |
| 6,585,716 B2 | 7/2003 | Altman |
| 6,606,517 B1 | 8/2003 | Park et al. |
| 6,609,027 B2 | 8/2003 | Kroll et al. |
| 6,623,473 B1 | 9/2003 | Ponzi |
| 6,623,474 B1 | 9/2003 | Ponzi |
| 6,643,546 B2 | 11/2003 | Mathis et al. |
| 6,650,940 B1 | 11/2003 | Zhu et al. |
| 6,702,744 B2 | 3/2004 | Mandrusov et al. |
| 6,702,777 B2 | 3/2004 | Haim et al. |
| 6,718,206 B2 | 4/2004 | Casavant |
| 6,766,190 B2 | 7/2004 | Ferek-Petric |
| 6,768,923 B2 | 7/2004 | Ding et al. |
| 6,801,807 B2 | 10/2004 | Abrahamson |
| 6,804,555 B2 | 10/2004 | Warkentin |
| 6,810,286 B2 | 10/2004 | Donovan et al. |
| 6,855,124 B1 | 2/2005 | Gonzalez et al. |
| 6,901,289 B2 | 5/2005 | Dahl et al. |
| 6,905,476 B2 | 6/2005 | Ponzi |
| 6,907,285 B2 | 6/2005 | Denker et al. |
| 6,909,920 B2 | 6/2005 | Lokhoff et al. |
| 6,915,169 B2 | 7/2005 | Flynn et al. |
| 6,931,286 B2 | 8/2005 | Sigg et al. |
| 6,937,897 B2 | 8/2005 | Min et al. |
| 7,027,876 B2 | 4/2006 | Casavant et al. |
| 7,039,462 B2 | 5/2006 | Pastore et al. |
| 7,096,051 B1 | 8/2006 | Alder |
| 7,113,825 B2 | 9/2006 | Pastore et al. |
| 7,130,682 B2 | 10/2006 | Stahmann et al. |
| 7,187,970 B2 | 3/2007 | Shemer et al. |
| 7,245,973 B2 | 7/2007 | Liu et al. |
| 7,257,443 B2 | 8/2007 | Pastore et al. |
| 7,280,872 B1 | 10/2007 | Mosesov et al. |
| 7,317,950 B2 | 1/2008 | Lee |
| 7,319,900 B2 | 1/2008 | Kim et al. |
| 7,359,837 B2 | 4/2008 | Drew |
| 7,392,095 B2 | 6/2008 | Flynn et al. |
| 7,395,042 B2 | 7/2008 | Alder |
| 7,400,931 B2 | 7/2008 | Mandrusov et al. |
| 7,460,914 B2 | 12/2008 | Mandrusov et al. |
| 7,512,440 B2 | 3/2009 | Ortega et al. |
| 7,529,584 B2 | 5/2009 | Laske et al. |
| 7,792,580 B2 | 9/2010 | Borowitz et al. |
| 7,817,784 B2 | 10/2010 | Wang et al. |
| 8,005,544 B2 | 8/2011 | Zhu et al. |
| 8,010,191 B2 | 8/2011 | Zhu et al. |
| 8,010,192 B2 | 8/2011 | Zhu et al. |
| 8,014,861 B2 | 9/2011 | Zhu et al. |
| 8,050,756 B2 | 11/2011 | Zhu et al. |
| 2001/0031986 A1 | 10/2001 | Hauck |
| 2001/0044619 A1 | 11/2001 | Altman |
| 2002/0010492 A1 | 1/2002 | Donovan et al. |
| 2002/0016615 A1 | 2/2002 | Dev et al. |
| 2002/0022863 A1 | 2/2002 | Hauck |
| 2002/0026228 A1 | 2/2002 | Schauerte |
| 2002/0049478 A1 | 4/2002 | Ding et al. |
| 2002/0058981 A1 | 5/2002 | Zhu et al. |
| 2002/0099413 A1 | 7/2002 | Mower |
| 2002/0120318 A1 | 8/2002 | Kroll et al. |
| 2002/0169484 A1 | 11/2002 | Mathis et al. |
| 2002/0183720 A1 | 12/2002 | Hill et al. |
| 2002/0193836 A1 | 12/2002 | Schmidt |
| 2002/0198583 A1 | 12/2002 | Rock et al. |
| 2003/0009145 A1 | 1/2003 | Struijker-Boudier |
| 2003/0032938 A1 | 2/2003 | Altman |
| 2003/0069625 A1 | 4/2003 | Ley et al. |
| 2003/0078625 A1 | 4/2003 | Casavant |
| 2003/0093104 A1 | 5/2003 | Bonner et al. |
| 2003/0105492 A1 | 6/2003 | Ding et al. |
| 2003/0105496 A1 | 6/2003 | Yu et al. |
| 2003/0109914 A1 | 6/2003 | Westlund et al. |
| 2003/0113303 A1 | 6/2003 | Schwartz |
| 2003/0125615 A1 | 7/2003 | Schwartz |
| 2003/0129750 A1 | 7/2003 | Schwartz |
| 2003/0163184 A1 | 8/2003 | Scheiner et al. |
| 2003/0171723 A1 | 9/2003 | Ponzi |
| 2003/0195470 A1 | 10/2003 | Ponzi |
| 2004/0006265 A1 | 1/2004 | Alhussiny |
| 2004/0064176 A1 | 4/2004 | Min et al. |
| 2004/0106958 A1 | 6/2004 | Mathis et al. |
| 2004/0122484 A1 | 6/2004 | Hatlestad et al. |
| 2004/0153127 A1 | 8/2004 | Gordon et al. |
| 2004/0186546 A1 | 9/2004 | Mandrusov et al. |
| 2004/0213770 A1 | 10/2004 | Seward et al. |
| 2004/0214182 A1 | 10/2004 | Sharma et al. |
| 2004/0215240 A1 | 10/2004 | Lovett et al. |
| 2004/0215249 A1 | 10/2004 | Corbucci |
| 2004/0215251 A1 | 10/2004 | Sharma et al. |
| 2004/0260374 A1 | 12/2004 | Zhang et al. |
| 2005/0049516 A1 | 3/2005 | Ideker |
| 2005/0075677 A1 | 4/2005 | Ganion et al. |

(56) References Cited

U.S. PATENT DOCUMENTS

| | | |
|---|---|---|
| 2005/0125041 A1 | 6/2005 | Min et al. |
| 2005/0136385 A1 | 6/2005 | Mann |
| 2005/0137671 A1 | 6/2005 | Liu et al. |
| 2005/0152516 A1 | 7/2005 | Wang et al. |
| 2005/0159725 A1 | 7/2005 | Tockman et al. |
| 2005/0203580 A1 | 9/2005 | Prentice et al. |
| 2005/0267557 A1 | 12/2005 | Flynn et al. |
| 2005/0277993 A1 | 12/2005 | Mower |
| 2006/0030810 A1 | 2/2006 | Mandrusov et al. |
| 2006/0064027 A1 | 3/2006 | Borowitz et al. |
| 2006/0104596 A1 | 5/2006 | Askins et al. |
| 2006/0116596 A1 | 6/2006 | Zhou et al. |
| 2006/0136001 A1* | 6/2006 | Ortega et al. ............... 607/9 |
| 2006/0142812 A1 | 6/2006 | Ortega et al. |
| 2006/0224197 A1 | 10/2006 | Havel et al. |
| 2006/0224224 A1 | 10/2006 | Muhlenberg et al. |
| 2006/0253156 A1 | 11/2006 | Pastore et al. |
| 2007/0027488 A1 | 2/2007 | Kaiser et al. |
| 2007/0060961 A1 | 3/2007 | Echt et al. |
| 2007/0093872 A1 | 4/2007 | Chirife et al. |
| 2007/0093874 A1 | 4/2007 | Chirife et al. |
| 2007/0129764 A1 | 6/2007 | Burnes |
| 2007/0232949 A1 | 10/2007 | Saksena |
| 2007/0233216 A1 | 10/2007 | Liu et al. |
| 2007/0239219 A1 | 10/2007 | Salo et al. |
| 2008/0262587 A1 | 10/2008 | Flynn et al. |
| 2008/0319496 A1 | 12/2008 | Zhu et al. |
| 2008/0319499 A1 | 12/2008 | Zhu et al. |
| 2008/0319500 A1 | 12/2008 | Zhu et al. |
| 2008/0319501 A1 | 12/2008 | Zhu et al. |
| 2009/0005830 A1 | 1/2009 | Zhu et al. |
| 2009/0005832 A1 | 1/2009 | Zhu et al. |
| 2009/0005846 A1 | 1/2009 | Zhu et al. |
| 2009/0054942 A1 | 2/2009 | Zhu et al. |
| 2009/0093859 A1 | 4/2009 | Ortega et al. |
| 2009/0093861 A1 | 4/2009 | Ortega et al. |
| 2009/0099619 A1 | 4/2009 | Lessmeier et al. |
| 2009/0105778 A1 | 4/2009 | Lee et al. |
| 2009/0259272 A1 | 10/2009 | Reddy et al. |
| 2010/0042176 A1 | 2/2010 | Snell |
| 2010/0318147 A1 | 12/2010 | Forslund et al. |
| 2011/0264158 A1 | 10/2011 | Dong et al. |
| 2011/0264168 A1 | 10/2011 | Dadd et al. |
| 2011/0307026 A1 | 12/2011 | Zhu et al. |
| 2011/1031995 | 12/2011 | Zhu et al. |

FOREIGN PATENT DOCUMENTS

| | | |
|---|---|---|
| DE | 3712082 A1 | 10/1988 |
| EP | 0042551 A1 | 12/1981 |
| EP | 0057877 A1 | 8/1982 |
| EP | 0282047 A2 | 9/1988 |
| EP | 0321764 A1 | 6/1989 |
| EP | 0452278 A2 | 10/1991 |
| EP | 0573275 A2 | 12/1993 |
| EP | 0591053 A1 | 4/1994 |
| EP | 0612538 A2 | 8/1994 |
| EP | 0620024 A1 | 10/1994 |
| EP | 0672431 A2 | 9/1995 |
| EP | 0709111 A2 | 5/1996 |
| EP | 1234597 A2 | 8/2002 |
| FR | 2465489 | 3/1981 |
| FR | 2575925 A1 | 7/1986 |
| FR | 2757773 A1 | 7/1998 |
| GB | 2240721 | 8/1991 |
| JP | 10-052507 A | 2/1998 |
| WO | WO-92/20401 A1 | 11/1992 |
| WO | WO-94/22525 A1 | 10/1994 |
| WO | WO-96/15665 A2 | 5/1996 |
| WO | WO-97/40883 A1 | 11/1997 |
| WO | WO-00/74773 A1 | 12/2000 |
| WO | WO-03/035170 A1 | 5/2003 |
| WO | WO-2005/011475 A2 | 2/2005 |
| WO | WO-2006/068880 A1 | 6/2006 |
| WO | WO-2008/063498 A1 | 5/2008 |
| WO | WO-2009/006321 A2 | 1/2009 |
| WO | WO-2009/006325 A1 | 1/2009 |
| WO | WO-2009/006327 A1 | 1/2009 |
| WO | WO-2009/006331 A1 | 1/2009 |
| WO | WO-2009/006339 A1 | 1/2009 |
| WO | WO-2009/078751 A1 | 6/2009 |
| WO | WO-2010/042910 A1 | 4/2010 |
| WO | WO-2010/071849 A2 | 6/2010 |
| WO | WO-2011139691 A1 | 11/2011 |
| WO | WO-2012125273 A2 | 9/2012 |

OTHER PUBLICATIONS

"U.S. Appl. No. 10/004,695, Notice of Allowance mailed Apr. 13, 2004", 7 pgs.

"U.S. Appl. No. 10/004,695, Response filed Mar. 9, 2004 to Non-Final Office Action mailed Dec. 22, 2003", 8 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement mailed Aug. 12, 2005", 6 pgs.

"U.S. Appl. No. 10/745,302, Response filed Dec. 14, 2006 to Non Final Office Action mailed Sep. 14, 2006", 13 pgs.

"U.S. Appl. No. 10/745,302, Response filed Dec. 23, 2005 to Non Final Office Action mailed Sep. 23, 2005", 15 pgs.

"U.S. Appl. No. 10/745,302, Restriction Requirement mailed Aug. 12, 2005", 7 pgs.

"U.S. Appl. No. 11/300,242, Final Office Action mailed Aug. 4, 2009", 9 pgs.

"U.S. Appl. No. 11/300,242, Non Final Office Action mailed May 12, 2011", 9 pgs.

"U.S. Appl. No. 11/300,242, Non-Final Office Action mailed Mar. 27, 2008", 8 pgs.

"U.S. Appl. No. 11/300,242, Response filed Feb. 4, 2010 to Final Office Action mailed Aug. 4, 2009", 11 pgs.

"U.S. Appl. No. 11/300,242, Response filed Apr. 2, 2009 to Restriction Requirement mailed Dec. 15, 2008", 8 pgs.

"U.S. Appl. No. 11/300,242, Response filed Sep. 12, 2011 to Non Final Office Action mailed May 12, 2011", 8 pgs.

"U.S. Appl. No. 11/300,242, Response filed Sep. 26, 2008 to Non-Final Office Action mailed Mar. 27, 2008", 10 pgs.

"U.S. Appl. No. 11/300,242, Restriction Requirement mailed Dec. 15, 2008", 10 pgs.

"U.S. Appl. No. 11/300,611, 312 Amendment filed Feb. 9, 2009", 9 pgs.

"U.S. Appl. No. 11/300,611, Non-Final Office Action mailed Mar. 20, 2008", 7 pgs.

"U.S. Appl. No. 11/300,611, Notice of Allowance mailed Jan. 26, 2009", 7 pgs.

"U.S. Appl. No. 11/300,611, PTO Response to 312 Amendment mailed Feb. 26, 2009", 3 pgs.

"U.S. Appl. No. 11/300,611, Response filed Sep. 22, 2008 to Non-Final Office Action mailed Mar. 20, 2008", 12 pgs "U.S. Appl. No. 12/147,293, Notice of Allowance mailed Apr. 8, 2011", 12 pgs.

"U.S. Appl. No. 12/147,293, Response filed Feb. 8, 2011 to Restriction Requirement mailed Oct. 8, 2010", 9 pgs.

"U.S. Appl. No. 12/147,293, Restriction Requirement mailed Oct. 8, 2010", 12 pgs.

"U.S. Appl. No. 12/147,317, Examiner Interview Summary mailed Mar. 15, 2011", 3 pgs.

"U.S. Appl. No. 12/147,317, Final Office Action mailed Oct. 12, 2011", 6 pgs.

"U.S. Appl. No. 12/147,317, Non-Final Office Action mailed Dec. 28, 2010", 7 pgs.

(56) References Cited

OTHER PUBLICATIONS

"U.S. Appl. No. 12/147,317, Response filed Jun. 27, 2011 to Non Final Office Action mailed Dec. 28, 2010", 11 pgs.
"U.S. Appl. No. 12/147,339, Notice of Allowance mailed Mar. 30, 2011", 9 pgs.
"U.S. Appl. No. 12/147,339, Notice of Allowance mailed Dec. 22, 2010", 8 pgs.
"U.S. Appl. No. 12/147,339, Response filed Oct. 20, 2010 to Restriction Requirement mailed Oct. 8, 2010", 7 pgs.
"U.S. Appl. No. 12/147,339, Restriction Requirement mailed Oct. 8, 2010", 7 pgs.
"U.S. Appl. No. 12/147,356, Notice of Allowance mailed Feb. 10, 2011", 17 pgs.
"U.S. Appl. No. 12/147,356, Notice of Allowance mailed Jun. 30, 2011", 15 pgs.
"U.S. Appl. No. 12/147,356, Response filed Nov. 10, 2010 to Restriction Requirement mailed Oct. 12, 2010", 9 pgs.
"U.S. Appl. No. 12/147,356, Restriction Requirement mailed Oct. 12, 2010", 7 pgs.
"U.S. Appl. No. 12/147,369, Non-Final Office Action mailed Sep. 10, 2010", 10 pgs.
"U.S. Appl. No. 12/147,369, Notice of Allowance mailed Apr. 21, 2011", 7 pgs.
"U.S. Appl. No. 12/147,369, Response filed Feb. 10, 2011 to Non Final Office Action mailed Sep. 10, 2010", 7 pgs.
"U.S. Appl. No. 12/147,376, Final Office Action mailed Apr. 20, 2011", 11 pgs.
"U.S. Appl. No. 12/147,376, Non Final Office Action mailed Oct. 3, 2011", 8 pgs.
"U.S. Appl. No. 12/147,376, Non-Final Office Action mailed Sep. 15, 2010", 9 pgs.
"U.S. Appl. No. 12/147,376, Response filed Feb. 15, 2011 to Non Final Office Action mailed Sep. 15, 2010", 9 pgs.
"U.S. Appl. No. 12/147,376, Response filed Aug. 22, 2011 to Final Office Action mailed Apr. 20, 2011", 8 pgs.
"U.S. Appl. No. 12/147,425, Non-Final Office Action mailed Sep. 15, 2010", 10 pgs.
"U.S. Appl. No. 12/147,425, Notice of Allowance mailed Apr. 19, 2011", 8 pgs.
"U.S. Appl. No. 12/147,425, Response filed Feb. 15, 2011 to Non Final Office Action mailed Sep. 15, 2010", 8 pgs.
"U.S. Appl. No. 12/249,454, Examiner Interview Summary mailed Feb. 22, 2012", 3 pgs.
"U.S. Appl. No. 12/249,454, Final Office Action mailed Nov. 23, 2011", 8 pgs.
"U.S. Appl. No. 12/249,454, Non Final Office Action mailed Apr. 6, 2011", 8 pgs.
"U.S. Appl. No. 12/249,454, Response filed Aug. 30, 2011 to Non Final Office Action mailed Apr. 6, 2011", 14 pgs.
"U.S. Appl. No. 12/249,479, Final Office Action mailed Dec. 2, 2011", 8 pgs.
"U.S. Appl. No. 12/249,479, Non Final Office Action mailed Apr. 5, 2011", 10 pgs.
"U.S. Appl. No. 12/249,479, Response filed Aug. 30, 2011 to Non Final Office Action mailed Apr. 5, 2011", 12 pgs.
"U.S. Appl. No. 12/249,508, Notice of Allowance mailed Feb. 14, 2012", 7 pgs.
"U.S. Appl. No. 12/249,508, Notice of Allowance mailed Oct. 5, 2011", 9 pgs.
"U.S. Appl. No. 12/249,508, Response filed Aug. 30, 2011 to Restriction Requirement mailed Jun. 30, 2011", 8 pgs.
"U.S. Appl. No. 12/249,508, Restriction Requirement mailed Jun. 30, 2011", 6 pgs.
"U.S. Appl. No. 12/412,608, Final Office Action mailed Nov. 21, 2011", 6 pgs.
"U.S. Appl. No. 12/412,608, Non Final Office Action mailed May 26, 2011", 8 pgs.
"U.S. Appl. No. 12/412,608, Response filed Sep. 26, 2011 to Non Final Office Action mailed May 26, 2011", 9 pgs.

"ATROSTIM Phrenic Nerve Stimulator", *Product Brochure*, AtroTech Oy, P.O. Box 28, FIN-33721 Tampere, Finland, (Jun. 2004), 2 pgs.
"Australian Application Serial No. 2005319498, First Examiner Report mailed May 27, 2010", 3 pgs.
"Australian Application Serial No. 2005319498, Response filed Feb. 21, 2011 to First Examiner Report mailed May 27, 2010", 11 pgs.
"Coating Process for Composite implants", Medical Materials Update, vol. 1, No. 12, (Jan. 1995), 3 pgs.
"European Application Serial No. 05849548,2, Communication and Supplementary Partial European Search Report mailed Feb. 29, 2008", 8 pgs.
"European Application Serial No. 05849548.2, Communication mailed Jun. 9, 2009", 3 pgs.
"European Application Serial No. 05849548.2, Office Action mailed Dec. 20, 2010", 4 pgs.
"European Application Serial No. 05849548.2, Response filed Jun. 29, 2011 to Non Final Office Action mailed Dec. 20, 2010", 9 pgs,
"European Application Serial No. 05849548.2, Response filed Dec. 16, 2009 to Communication mailed Jun. 9, 2009", 10 pgs.
"European Application Serial No. 08772198.1, Office Action mailed Sep. 13, 2010", 6 pgs.
"European Application Serial No, 08772198.1, Response filed Mar. 31, 2011 to Communication mailed Sep. 30, 2010", 11 pgs.
"European Application Serial No. 08781107.1, Invitation Pursuant to Rule 63(1) EPC mailed Jul. 13, 2010", 3 pgs.
"European Application Serial No. 08781107.1, Communication dated Feb. 9, 2010", 2 pgs
"European Application Serial No. 08781107.1, Extended European Search Report mailed Nov. 25, 2010", 6 pgs.
"European Application Serial No. 08781107.1, Response filed Mar. 5, 2010 to Communication dated Feb. 9, 2010", 2 pgs.
"European Application Serial No. 08781107.1, Response filed Jun. 14, 2011 to Communication mailed Dec. 14, 2010", 10 pgs.
"European Application Serial No. 08781107.1, Response filed Sep. 22, 2010 to the Invitation to Rule 63(1)", 11 pgs.
"European Application Serial No, 08796045.6, European Search Report mailed Sep. 21, 2010", 6 pgs.
"European Application Serial No. 08796045.6, Response filed Apr. 15, 2011 to Communication dated Oct. 8, 2010", 10 pgs.
"Implant Attaches to Bone by Chemical Bond", *Medical Materials Update*, vol. 4, No. 7, (Aug. 1997), 2 pgs.
"International Application Serial. No. PCT/US05/45044, International Search Report mailed May 2, 2006", 1 pg.
"International Application Serial No. PCT/US05/45044, Written Opinion mailed May 2, 2006", 3 pgs.
"International Application Serial No. PCT/US08/68618, International Search Report mailed Nov. 26, 2008", 2 pgs.
"International Application Serial No. PCT/US08/68618, Written Opinion mailed Nov. 26, 2008", 6 pgs.
"International Application Serial No. PCT/US08/68627, International Search Report mailed Sep. 10, 2008", 1 pg.
"International Application Serial No. PCT/US08/68627, Written Opinion mailed Sep. 10, 2008", 4 pgs.
"International Application Serial No. PCT/US08/68630, International Search Report mailed Sep. 10, 2008", 1 pg.
"International Application Serial. No. PCT/US08/68630, Written Opinion mailed Sep. 10, 2008", 4 pgs.
"International Application Serial No. PCT/US08/68632, International Search Report mailed Sep. 11, 2008", 2 pgs.
"International Application Serial No. PCT/US08/68632, Written Opinion mailed Sep. 11, 2008", 4 pgs.
"International Application Serial No. PCT/US08/68647, International Search Report mailed Sep. 22, 2008", 2 pgs.
"International Application Serial No. PCT/US08/68647, Written Opinion mailed Sep. 22, 2008", 4 pgs.
"International Application Serial No. PCT/US08/68654, International Search Report mailed Sep. 22, 2008", 2 pgs.
"International Application Serial No. PCT/US08/68654, Written Opinion mailed Sep. 22, 2008", 4 pgs.
"International Application Serial No. PCT/US2008/068635, International Search Report mailed Sep. 9, 2008", 3 pgs.

(56) References Cited

OTHER PUBLICATIONS

"International Application Serial No. PCT/US2008/068635, Written Opinion mailed Sep. 9, 2008", 4 pgs.
"International Application Serial No. PCT/US2009/060293, International Preliminary Report on Patentability mailed Apr. 12, 2011", 10 pgs.
"International Application Serial No. PCT/US2009/060293, International Search Report mailed Mar. 10, 2010", 6 pgs.
"International Application Serial No. PCT/US2009/060293, Invitation to Pay Additional Fee mailed Dec. 18, 2009", 5 pgs.
"International Application Serial No. PCT/US2009/060293, Written Opinion mailed Mar. 10, 2010", 10 pgs
"International Application Serial No. PCT/US2009/068859, International Search Report mailed Jul. 5, 2010", 7 pgs.
"International Application Serial No. PCT/US2009/068859, Invitation to Pay Additional Fee mailed Apr. 15, 2010", 6 pgs.
"International Application Serial No. PCT/US2009/068859, Written Opinion mailed Jul. 5, 2010", 12 pgs.
"International Application Serial No. PCT/US2011/033944, International Search Report mailed Sep. 8, 2011", 5 pgs.
"International Application Serial No. PCT/US2011/033944, Written Opinion mailed Sep. 8, 2011", 9 pgs.
"Japanese Application Serial No. 2007-548289, Final Office Action dated Aug. 2, 2011", (w/ English Translation), 5 pgs.
"Japanese Application Serial No. 2007-548289, Office Action mailed Nov. 24, 2010", (w/ English Translation), 7 pgs.
"Japanese Application Serial No. 2007-548289, Response filed May 20, 2011 to Office Action mailed Nov. 24, 2010", (w/ English Translation of Amended Claims), 9 pgs.
"Japanese Application Serial No. 2007-548289, Response filed Oct. 26, 2011 to Office Action mailed Aug. 3, 2011", (w/ English Translation of Amended Claims), 10 pgs.
"Victrex's PEEK Used for Dialysis Machines", *Medical Material's Update*, vol. 3, No. 3, (Apr. 1996), pp. 1-2.
Alboni, P., "Bundle Branch Blocks Anatomically Located in the His Bundle", *Italian Cardiology Journal*, 10(12), (w/ English Translation thereof, followed by Italian publication), (1980), 1583-1587.
Al-Khadra, A., et al., "The Role of Electroporation in Defibrillation", *Circulation Research*, 87(9), (Oct. 2000), 797-804.
Avitall, B., et al., "Iontophoretic Transmyocardial Drug Delivery. A Novel Approach to Antiarrhythmic Drug Therapy", *Circulation*, 85(4), (1992), 1582-1593.
Barba-Pichardo, Rafael, et al., "Permanent His-Bundle Pacing in Patients With Infra-Hisian Atrioventricular Block", *Rev Esp Cardiol.* 59(6), (Mar. 9, 2006), 553-558.
Barton, A. J., et al., "Bacterial Adhesion to Orthopedic Implant Polymers", *J. Biomed. Mat. Res.*, 30(3), (Mar. 1996), 403-410.
Bonanno, C., et al., "Effect on QRS Duration and Feasibility of Septal and Multisite Right Ventricular Pacing", *Cardiostimolazione*, 14(3), (Abstract Only), (Sep. 1996), p. 195
Buckingham, T. A.., et al., "Acute Hemodynamic Effects of Atrioventricular Pacing at Differing Sites in the Right Ventricle Individually and Simultaneously". *PACE*, 20[Pt. I], (Apr. 1997), 909-915.
Cantu, F., et al., "Validation of Criteria for Selective His Bundle and Para-Hisian Permanent Pacing", *PACE*, vol. 29, (Dec. 2006), 1326-1333.
Cantu, Francesco, et al., "A Methodical Approach to Validate Selective His Bundle and para-Hisian Permanent Pacing", [abstract] *Oasis*, (2006), 1 pg.
Catanzariti, Domenico, et al., "Permanent His Bundle Pacing Does Not Induce Ventricular Dyssynchrony. An Echocardiographic Intrapatient Study of Comparison with Conventional Pacing", [abstract] *Oasis*, (2006), 1 pg.
Chiu, L., et al., "Method for One-Click Deployment and or Configuration of Real-Time Software System Modifications", U.S. Appl. No. 60/558,921, filed Apr. 2, 2004, 8 pgs.
Chudzik, Michal, "Ventricular Endocardial Right Bifocal Stimulation in Treatment of Severe Dilated Cardiomyopathy Heart Failure in Patients with Unsuccessful Biventricular Pacemaker Implantation", [abstract CP07] *Europace Supplements*, vol. 7, (May 2005), 1 pg.
Deshmukh, P., et al., "Permanent, Direct His-Bundle Pacing: A Novel Approach to Cardiac Pacing in Patients With Normal His-Purkinje Activation", *Circulation*, 101(8), (Feb. 29, 2000), 869-877.
Deshmukh, P. M., et al., "Direct His-Bundle Pacing: Present and Future", *PACE*, vol. 27, Part II, (Jun. 2004), 862-870.
Dong, Y., et al., "His-Bundle Capture Verification and Monitoring". U.S. Appl. No. 61/328,248, filed Apr. 27, 2010, 40 pgs.
El-Sherif, N., et al., "Normalization of Bundle Branch Block Patterns by Distal His Bundle Pacing: Clinical and Experimental Evidence of Longitudinal Dissociation in the Pathologic His Bundle", *Circulation*, 57(3) (Mar. 1978), 473-483.
Flynn, D. M, et al., "Extendable and Retractable Lead Having a Snap-Fit Terminal Connector", U.S. Appl. No. 11/173,664, filed Jul. 1, 2005, 53 pgs.
Furman, S., et al., "Chapter 5—Permanent Pacemaker Implementation", *A Practice of Cardiac Pacing*, Futura Publishing Co., Inc. Mount Kisco, NY, (1986), 97-127.
Genc, S., et al., "Methodology for Locking Feature Selection in Integral Snap-Fit Assembly", *Proceedings of DETC '97, 1997 ASME Engineering Technical Conferences*, (Sep. 1997), 1-11.
Golia, P., et al., "Multisite Pacing of Right Ventricle in Heart Failure: Echocardiographic Evaluation", [Abstract] *Cardiostimolazione*, vol. 14, No. 3, (Sep. 1996), 5 pgs.
Grosfeld, M. J.W., et al., "Testing a New Mechanism for Left Interventricular Septal Pacing: The Transseptal Route", *Europace*, vol. 4, (Oct. 2002), 439-444.
Ha, S. W. et al., "Plasma-Sprayed Hydroxylapatite Coating on Carbon Fibre Reinforced Thermoplastic Composite Materials", *J. Mater. Sci. Mater. Med.*, vol. 5, No. 6-7, (1994), pp. 481-484.
Hummel, J. D., et al., "Augmentation of Cardiac Output by Anodai Pacing", [Abstract] *Circulation*, 90(No. 4, Part 2), (Oct. 1994), p. I-69.
Ingle, F., et al., "Lead Motion Sensing Via Cable Microphonics", U.S. Appl. No. 61/359,430, filed Jun. 29, 2010, 52 pgs.
Jockisch, K. A., et al., "Biological Response to Chopped-Carbon-Fiber-Reinforced Peek", *J. Biomed. Mater. Res.*, 26(2), (1992), 133-146.
Kanno, S., et al., "Establishment of a simple and practical procedure applicable to therapeutic angiogenesis", *Circulation*, 99(20), (May 25, 1999), 2682-2687.
Kavanagh, K. M., et al., "Monophasic Versus Biphasic Cardiac Stimulation: Mechanism of Decreased Energy Requirements", *PACE*, 13(10), (Oct. 1990), 10 pgs.
Kaye, D. M., et al., "Frequency-dependent activation of a constitutive nitric oxide synthase and regulation of contractile function in adult rat ventricular myocytes", *Circulation Research*, 78(2), (Feb. 1996), 217-224.
Knapp, C. P., et al., "Snap Fit Terminal Connector", U.S. Appl. No. 09/184,226, filed Nov. 2, 1998, 39 pgs.
Kutarski, A., et al., "Factors Influencing Differences of RVA & RVOT Pacing Hemodynamic Effects", [abstract CP05] *Europace Supplements*, vol. 7, (May 2005), p. 288.
Kutarski, A., et al., "Right Ventricular Outflow Tract and Dual Site Right Ventricular Pacing—The Comparison With Apex Pacing", [abstract CP08] *Europace Supplements*, vol. 7 (May 2005), p. 288.
Labhasetwar, V., et al., "Iontophoresis for Modulation of Cardiac Drug Delivery in Dogs", *Proc. Natl. Acad. of Sci. USA*, (Mar. 28, 1995), 2612-2616.
Lazarus, A., et al., "Reduction in Energy Pacing Thresholds by Overlapping Biphasic Stimulation Versus Conventional Bipolar Pacing", *PACE*, vol. 21, (Nov. 1998), 6 pgs.
Lin, T. W., et al., "Glass Peek Composite Promotes Proliferation and Osteocalcin of Human Osteoblastic Cells", *J. Biomed. Mater. Res.*, 36(2), (1997), 137-144.
Lupi, G., et al., "Effects of Right Ventricular Pacing on Intra-Left Ventricular Electromechanical Activation in Patients with Native Narrow QRS.", *American Journal of Cardiology*, vol. 98, (2006), 219-222.
MacNair, R., et al., "The Response of Primary Rat and Human Osteoblasts and an Immortalized Rat Osteoblast Cell Line to

(56) References Cited

OTHER PUBLICATIONS

Orthopaedic Materials: Comparative Sensitivity of Several Toxicity Indices", *J. Mater. Sci. Mater. Med.*, 8(2), (1997), 105-111.

Manolis, A. S., "The Deleterious Consequences of Right Ventricular Apical Pacing: Time to Seek Alternate Site Pacing", *PACE*, vol. 29, (Mar. 2006), 298-315.

Mansourati, J., et al., "Left ventricular-based pacing in patients with chronic heart failure: comparison of acute hemodynamic benefits according to underlying heart disease", *Eur J Heart Fail.*, 2(2), (Jun. 2000), 195-199.

Meyer, M. R., et al., "Long-Term Durability of the Interface in FRP Composites After Exposure to Simulated Physiologic Saline Environments", *J. Biomed. Mater. Res.*, 28(10), (1994), 1221-1231.

Mond, Harry G., et al., "The Right Ventricular Outflow Tract: The Road to Septal Pacing", *PACE*, vol. 30, (Apr. 2007), 482-491.

Morina-Vazquez, Pablo, et al., "Cardiac Resynchronization Through Selective His Bundle Pacing in a Patient with the So-Called InfraHis Atrioventricular Block", *Pace*, vol. 28, (Jul. 2005), 726-729.

Morrison, C., et al., "In Vitro Biocompatibility Testing of Polymers for Orthopaedic Implants Using Cultured Fibroblasts and Osteoblasts", *Biomaterials*, 16(13), (1995), 987-992.

Narula, O. S., "Longitudinal Dissociation in the His Bundle. Bundle Branch Block Due to Asynchronous Conduction Within The His Bundle in Man", *Circulation*, 56(6), (Dec. 1977), 996-1006.

Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", Journal of the *American College of Cardiology*, 47(10), (May 16, 2006), 1938-1945.

Padeletti, Luigi, et al., "Physiologic Pacing: New Modalities and Pacing Sites", *PACE*, vol. 29, Supplement 2, (Dec. 2006), S73-S77.

Pastore, G., et al., "Different Degree of Ventricular Dyssyncrony Induced by Right Apical, Hissian and Para Hissian Ventricular Pacing", [abstract] *Oasis*, (2006), 1 pg.

Pastore, G., et al., "Direct His-Bundle Pacing Preserves the Normal Left Activation Sequence: An Acute Echocardiographic Study", [abstract] *Oasis*, (2006), 1 pg.

Puech, P., et al., "Narrowing and normalization of QRS stimulation of the His bundle in complete left bundle branch block.", *Scholarly Journal of the French Cardiology Society*. vol. 72, No. 8, (w/ English Translation thereof, followed by French publication), (Aug. 1979), 815-824.

Qu, J, et al., "GCN2 overepression in newborn and adult ventricular myocytes: distinct effects on gating and excitability", *Circ. Res.*, vol. 89 (1), (Jul. 6, 2001), e8-e14.

Qu, J, et al., "Sympathetic innervation alters activations of pacemaker current (If) in rat ventricle", *J. Physiol*, 526 Pt 3, (Aug. 1, 2000), 561-569.

Ravazzi, A., et al., "Improvement of Interventricular Activation Time Using Biphasic Pacing Pulses at Different Sites on Right Ventricle Septal Wall", *Progress in Biomedical Research*, 4(3), (Jun. 1999), 248-253.

Reddy, G. S., "Bundle of His Stimulation System", U.S. Appl. No. 61/045,168, filed Apr. 15, 2008, 37 pgs.

Saksena, S., et al., "Chapter 9—Pacemaker Implantation Techniques", *Electrical Therapy for Cardiac Arrhythmias*, W.B. Saunders Co., Philadelphia, PA, (1990), pp. 173, 181-183.

Scheinman, M. M., et al., "Long-Term His-Bundle Pacing and Cardiac Function", *Circulation*, 101(8), (2000), 836-837.

Shoenfeld, M. H., "Alternative Site Pacing to Promote Cardiac Synchrony: Has Conventional Pacing Become Unconventional?", *Journal of the American College of Cardiology*, 47(10), (2006), 1946-1948.

Shi, W, et al., "Distribution and prevalence of hyperpolarization-activated cation channel (HCN) mRNA expression in cardiac tissues", *Circ. Res.*, vol. 85(1), (Jul. 9, 1999), el-6.

Sotobata, I., et al., "Population distribution of Frank-vectorcardiographic measurements of healthy Japanese men", *Japanese Circulation Journal*, 39(8), (1975), 895-903.

Soyer, J., et al., "Experimental Characterisation of a Carbon/PEEK Hip Prothesis in Fatigue", *Chirurgie*, 121, (1996), 658-663.

Sweeney, M. O., et al., "Adverse Effect of Ventricular Pacing on Heart Failure and Atrial Fibrillation Among Patients with Normal Baseline QRS Duration in a Clinical Trial of Pacemaker Therapy for Sinus Node Dysfunction", *Circulation*, 107(23), (2003), 2932-2937.

Sweeney, M. O., et al., "Heart Failure During Cardiac Pacing", *Circulation*, 113(17), (2006), 2082-2088.

Takatsuki, et al., "Clinical Implications of "pure" Hisian pacing in addition to para-Hisian pacing for the diagnosis of supraventricular tachycardia", *Heart Rhythm* 3(12), (Dec. 8, 2006), 1412-1418.

Tanabe, M., et al., "Biventricular Pacing Worsened Dyssynchrony in Heart Failure Patient with Right-Bundle Branch Block", *International Journal of Cardiology*, 138(3), (available online Aug. 15, 2008 / epub doi:10.1016/i.ijcard.2008.06,063 ), (2010), e47-e50.

Thakral, A, et al., "Effects of anodal vs. cathodal pacing on the mechanical performance of the isolated rabbit heart", *J. Appl Physiol.*, 89(3), (Sep. 2000), 1159-1164.

Tse, Hung-Fat, et al., "Selection of Permanent Ventricular Pacing Site: How Far Should We Go?", *Journal of the American College of Cardiology*, 48(8), (Sep. 26, 2006), 1649-1651.

Van Gelder, B. M., et al., "Hemodynamic Effect of RV Apex vs RV Septum Pacing in a Monoventricular and Biventricular Configuration in Patients with Heart Failure", [abstract CP06] *Europace Supplements*, vol. 7, (May 2005), p. 288.

Victor, F., et al., "A Randomized Comparison of Permanent Septal Versus Apical Right Ventricular Pacing: Short-Term Results", *Journal of Cardiovascular Electrophysiology*, 17(3), (Mar. 2006), 238-242.

Wang, S. C.-J., et al., "Improved Method and System for Managing Voice Prompt Recordings Prior to Deployment", U.S. Appl. No. 60/532,271, filed Dec. 23, 2003, 12 pgs.

Wenz, L. M., et al., "In Vitro Biocompatibility of Polyetheretherketone and Polysulfone Composites", *J. Biomed. Mater. Res.*, 26(2), (1990), 207-215.

Winckels, S. K. G., et al., "High-Septal Pacing Reduces Ventricular Electrical Remodeling and Proarrhythmia in Chronic Atrioventricular Block Dogs", *Journal of the American College of Cardiology*, 50(9), (Aug. 28, 2007), 906-913.

Yu, H., et al., "MinK-related peptide 1: A β subunit for the HCN ion channel subunit family enhances expression and speeds activation", *Circ. Res.*, 88(12), (Jun. 22, 2001), e84-e87.

Zanon, F., et al., "A Feasible Approach for Direct His-Bundle Pacing Using a New Steerable Catheter to Facilitate Precise Lead Placement", *Journal of Cardiovascular Electrophysiology*, 17(1), (Jan. 2006), 29-33.

Zanon, F., et al., "A New Technique for Direct His-Bundle Pacing: Acute and Mid-Term Electrical Data Results", [abstract] *Oasis*, (2006), 1 pg.

Zanon, F., et al., "Direct His Bundle Pacing Preserves Coronary Perfusion Compared With Right Ventricular Apical Pacing: A Prospective, Cross-Over Mid-Term Study", *Europace*, vol. 10, (2008), 580-587.

Zhang, Y., et al., "His Electrogram Alternans Reveal Dual-Wavefront Inputs Into and Longitudinal Dissociation Within the Bundle of His", *Circuiation*,104(7), (2001), 832-838.

U.S. Appl. No. 13/645,464, filed Oct. 4, 2012, Ventricular Pacing.

U.S. Appl. No. 13/875,681, filed May 2, 2013, Apparatus for Treating the Physiological Electric Conduction of the Heart.

U.S. Appl. No. 13/688,859, filed Nov. 29, 2012, Devices and Methods for Steering Electrical Stimulation in Cardiac Rhythm Management.

U.S. Appl. No. 13/862,776, filed Apr. 15, 2013, Methods, Devices and Systems for Cardiac Rhythm Management Using an Electrode Arrangement.

U.S. Appl. No. 13/650,444, filed Oct. 12, 2012, Methods, Devices and Systems for Single-Chamber Pacing Using a Dual-Chamber Pacing Device.

U.S. Appl. No. 13/094,416, filed Apr. 26, 2011, His-Bundle Capture Verification and Monitoring.

U.S. Appl. No. 13/404,814, filed Feb. 24, 2012, His Capture Verification Using Electro-Mechanical Delay.

(56) References Cited

OTHER PUBLICATIONS

"U.S. Appl. No. 12/147,317, Response filed Apr. 11, 2012 to Final Office Action mailed Oct. 12, 2011", 8 pgs.
"U.S. Appl. No. 12/147,376 , Response filed Feb. 29, 2012 to Non Final Office Action mailed Oct. 3, 2011", 6 pgs.
"U.S. Appl. No. 12/249,454, Non Final Office Action mailed Sep. 4, 2012", 8 pgs.
"U.S. Appl. No. 12/249,454, Response filed Apr. 2, 2012 to Final Office Action mailed Nov. 23, 2011", 12 pgs.
"U.S. Appl. No. 12/249,454, Response filed Dec. 4, 2012 to Non Final Office Action mailed Sep. 4, 2012", 12 pgs.
"U.S. Appl. No. 12/249,479, Non Final Office Action mailed Sep. 4, 2012", 7 pgs.
"U.S. Appl. No. 12/249,479, Response filed Apr. 2, 2012 to Final Office Action mailed Dec. 2, 2011", 9 pgs.
"U.S. Appl. No. 12/249,479, Response filed Dec. 4, 2012 to Non Final Office Action mailed Sep. 4, 2012", 9 pgs.
"U.S. Appl. No. 12/412,608, Response filed Apr. 18, 2012 to Final Office Action mailed Nov. 21, 2011", 7 pgs.
"U.S. Appl. No. 13/094,416 , Response filed Apr. 15, 2013 to Non Final Office Action mailed Dec. 14, 2012", 14 pgs.
"U.S. Appl. No. 13/094,416, Non Final Office Action mailed Dec. 14, 2012", 13 pgs.
"U.S. Appl. No. 13/211,937 , Response filed Apr. 11, 2013 to Non Final Office Action mailed Jan. 15, 2013", 8 pgs.
"U.S. Appl. No. 13/211,937, Non Final Office Action mailed Jan. 15, 2013", 7 pgs.
"U.S. Appl. No. 13/217,776 , Response filed Apr. 11, 2013 to Non Final Office Action mailed Jan. 15, 2013", 9 pgs.
"U.S. Appl. No. 13/217,776, Non Final Office Action mailed Jan. 15, 2013", 6 pgs.
"U.S. Appl. No. 13/404,814, Non Final Office Action mailed Jul. 16, 2013", 9 pgs.
"U.S. Appl. No. 13/688,859, Non Final Office Action mailed Jun. 20, 2013", 6 pgs.
"Australian Application Serial No. 2009327369, First Examination Report mailed Jul. 19, 2012", 3 pgs.
"European Application Serial No. 05849548.2, Office Action mailed Jan. 16, 2013", 3 pgs.
"European Application Serial No. 08796045.6, Office Action mailed Jan. 4, 2012", 4 pgs.
"European Application Serial No. 08796045.6, Response filed May 14, 2012 to Office Action mailed Jan. 4, 2012", 8 pgs.
"International Application Serial No. PCT/US2011/033944, International Preliminary Report on Patentability mailed Nov. 8, 2012", 9 pgs.
"International Application Serial No. PCT/US2012/026571, International Search Report mailed Oct. 18, 2012", 4 pgs.
"International Application Serial No. PCT/US2012/026571, Written Opinion mailed Oct. 18, 2012", 7 pgs.
"Japanese Application No. 2010-515198, Non Final Office Action dated Jul. 2, 2013", With English Translation, 14.
"Japanese Application Serial No. 2007-548289, Office Action mailed Mar. 6, 2012", (w/ English Translation), 3 pgs.
"Japanese Application Serial No. 2007-548289, Office Action mailed Nov. 6, 2012", With English Translation, 3 pgs.
"Japanese Application Serial No. 2010-515189, Office Action mailed Feb. 12, 2013", With English Translation, 9 pgs.
"Japanese Application Serial No. 2010-515196, Office Action mailed Jan. 15, 2013", With English Translation, 8 pgs.
"Japanese Application Serial No. 2010-515198, Office Action mailed Feb. 12, 2013", With English Translation, 16 pgs.
"Japanese Application Serial No. 2010-515198, Response filed Apr. 24, 2013 to Office Action mailed Feb. 12, 2013", With English Claims, 7 pgs.
"Japanese Application Serial No. 2011-531237, Office Action mailed Jan. 15, 2013", With English Translation, 7 pgs.
"Japanese Application Serial No. 2011-542513, Office Action mailed Jan. 15, 2013", With English translation, 6 pgs.
"Japanese Application Serial No. 2011-542513, Response filed Apr. 12, 2013 to Non Final Office Action dated Apr. 12, 2013", With English Claims, 10.
Arcot-Krishnamurthy, S., et al., "Timing for His-Bundle Pacing", U.S. Appl. No. 13/277,617, filed Oct. 20, 2011, 40 pgs.
Zhu, Q., et al., "Methods, Devices and Systems for Cardiac Pacing Therapies Using Intrinsic Activity", U.S. Appl. No. 61/139,117, filed Dec. 19, 2008, 22 pgs.
US 6,875,206, 04/2005, Ponzi (withdrawn)

* cited by examiner

DEVICES, METHODS, AND SYSTEMS INCLUDING CARDIAC PACING

CLAIM OF PRIORITY

This application is a U.S. National Stage Filing under 35 U.S.C. §371 and claims the benefit of priority under 35 U.S.C. §120 to International Patent Application Serial No. PCT/US2009/068859, filed Dec. 18, 2009, and published as WO 2010/071849 A2 on Jun. 24, 2010, and republished on Aug. 19, 2010 as WO 2010/071849 A3, which claims the benefit of priority under 35 U.S.C. §119(e) of the following, each of which is incorporated by reference herein in its entirety, and the benefit of priority of each of which is claimed herein:

1. Zhu et al., U.S. Provisional Patent Application No. 61/139,094 entitled METHODS, DEVICES AND SYSTEMS FOR CARDIAC PACING IN PATIENTS WITH PRESERVED EJECTION FRACTION, assigned to Action Medical, Inc., and filed on Dec. 19, 2008, expired;

2. Zhu et al., U.S. Provisional Patent Application No. 61/139,109 entitled METHODS, DEVICES AND SYSTEMS FOR CARDIAC PACING CONTROL RESPONSIVE TO FEEDBACK SIGNALS, assigned to Action Medical, Inc., and filed on Dec. 19, 2008, expired;

3. Zhu et al., U.S. Provisional Patent Application No. 61/139,117 entitled METHODS, DEVICES AND SYSTEMS FOR CARDIAC PACING THERAPIES USING INTRINSIC ACTIVITY, assigned to Action Medical, Inc., and filed on Dec. 19, 2008, expired;

4. Zhu et al., U.S. Provisional Patent Application No. 61/139,126 entitled METHODS, DEVICES AND SYSTEMS USING CARDIAC PACING THRESHOLDS, assigned to Action Medical, Inc., and filed on Dec. 19, 2008, expired;

5. Zhu et al., U.S. Provisional Patent Application No. 61/139,197 entitled METHODS, DEVICES AND SYSTEMS FOR USE WITH A CARDIAC PACING CATHETER, assigned to Action Medical, Inc., and filed on Dec. 19, 2008, expired;

6. Zhu et al., U.S. Provisional Patent Application No. 61/139,211 entitled METHODS, DEVICES AND SYSTEMS FOR USE WITH A PACING ELECTRODE AND ATTACHMENT MECHANISM, assigned to Action Medical, Inc., and filed on Dec. 19, 2008, expired;

7. Zhu et al., U.S. Provisional Patent Application No. 61/139,181 entitled METHODS, DEVICES AND SYSTEMS FOR USE WITH PACING ELECTRODES AND DELIVERY CATHETER, assigned to Action Medical, Inc., and filed on Dec. 19, 2008, expired;

8. Zhu et al., U.S. Provisional Patent Application No. 61/139,220 entitled METHODS, DEVICES AND SYSTEMS FOR ANTITACHYCARDIA PACING, assigned to Action Medical, Inc., and filed on Dec. 19, 2008, expired;

9. Zhu et al., U.S. Provisional Patent Application No. 61/139,226 entitled METHODS, DEVICES AND SYSTEMS FOR DELIVERY OF PACING LEADS FOR CARDIAC PACING, assigned to Action Medical, Inc., and filed on Dec. 19, 2008, expired;

10. Zhu et al., U.S. Provisional Patent Application No. 61/139,236 entitled METHODS, DEVICES AND SYSTEMS FOR ATRIOVENTRICULAR DELAY CONTROL, assigned to Action Medical, Inc., and filed on Dec. 19, 2008, expired; and 11. Zhu et al., U.S. Provisional Patent Application No. 61/139,249 entitled METHODS, DEVICES AND SYSTEMS FOR CHRONIC CARDIAC PACING, assigned to Action Medical, Inc., and filed on Dec. 19, 2008, expired.

BACKGROUND

Pacemakers are perhaps the most well known devices that provide chronic electrical stimulus, such as cardiac rhythm management. Modern pacemakers are designed to be implanted within a patient receiving the medical therapy. Other examples of cardiac stimulators include implantable cardiac defibrillators (ICDs) and implantable devices capable of performing pacing and defibrillating functions. Such implantable devices provide electrical stimulation to selected portions of the heart in order to treat disorders of cardiac rhythm. An implantable pacemaker paces the heart with timed pacing pulses. The pacing pulses can be timed relative to other pacing pulses or to sensed (intrinsic) electrical activity. If functioning properly, the pacemaker enforces a minimum heart rate to make up for the heart's inability to pace itself at an appropriate rhythm for metabolic demand. Some pacing devices synchronize pacing pulses delivered to different areas of the heart in order to coordinate the contractions. Coordinated contractions allow the heart to pump efficiently to provide sufficient cardiac output. Clinical data has shown that cardiac resynchronization, achieved through synchronized biventricular pacing, results in a significant improvement in cardiac function. Cardiac resynchronization therapy improves cardiac function in heart failure patients. Heart failure patients have reduced autonomic balance, which is associated with LV (left-ventricular) dysfunction and increased mortality.

Commonly treated conditions relate to the heart beating too fast or too slow. When the heart beats too slow, often leading to a condition referred to as bradycardia, pacing can be used to increase the intrinsic heart rate and correct the condition. When the heart beats too fast, often due to a condition referred to as tachycardia, intrinsic electrical stimulus of the heart itself, in the presence of certain myocardial substrate modifications (e.g., infarcted or non-conducting areas), can find a circuit that allows them to re-enter into the original activation circuit and re-trigger a new activation. These re-entrant circuits can lead to very fast heart rates that can be undesirable and even fatal. To correct for this condition, anti-tachycardia pacing (ATP) at rates higher than the tachyarrhythmia rates can be used to regain control of the heart rhythm by using specialized sequences of pulses and trains of pulses. Once the system delivering the antitachycardia fast pacing takes control of the heart, it can gradually reduce its pacing rate in the hopes that the normal sinus rhythm will take control again, and reduce the intrinsic heart rate. Antitachycardia pacing is generally used in combination with an implantable defibrillator, because the pacing burst could accelerate the arrhythmia into ventricular fibrillation.

When pacing for bradycardia, percutaneously placed pacing electrodes can be positioned in the right-side chambers (right atrium or right ventricle) of the heart. Access to such chambers is readily available through the superior vena cava, the right atrium, the tricuspid valve and then into the right ventricle. Pacing of both the right atrium and right ventricle was developed. Such dual chamber pacing resulted in better hemodynamic output than right ventricle-only pacing. In addition to treating bradycardia, dual chamber pacing maintained synchrony between the atrial and ventricular chambers.

Electrode placement in the left ventricle is normally avoided, where access is not as direct as in right ventricle placement. Moreover, emboli risk in the left ventricle is greater than in the right ventricle. Emboli that might develop in the left ventricle by reason of the electrode placement have direct access to the brain via the ascending aorta from the left ventricle. This could result in stroke.

Overview

Recent clinical evidence suggests that conventional ventricular pacing from the apex of the right ventricle can create asynchronous contraction of the left and right ventricles, thereby resulting in inefficient mechanical contraction and reduced hemodynamic performance. Long term conventional right ventricular apex pacing may be associated with an increased tendency of developing and/or worsening heart failure.

In clinical practice, anti-tachycardia pacing can be delivered using a defibrillation lead tip that is located in an apex of the right ventricle. An example of an implementation of a defibrillation lead has two coils. One coil is located inside the right ventricle, and the other is located in the atrium or superior vena cava. Often, the return electrode for the anti-tachycardia pacing signal is either a ring located distal to the end of one of the defibrillation coils or the can of the implantable defibrillator. The intent is for the pacing signal to overtake the tachycardia by pacing the rate at a higher rate than the rate of the existing tachycardia, thus placing the myocites in refractory and stopping the re-entrant loop from re-exiting the tachycardia. Once the high rate anti-tachycardia pacing burst is stopped, the heart is expected to go back to normal sinus rhythm. One problem, however, is that the efficacy of this approach is not 100%. It is believed that a reason for this lack of 100% success is the presence of conduction delays that don't allow the pacing stimulus to (fully) take control of the heart even when the pacing rate is higher than the tachycardia rate. In particular, it is believed that the propagation of the pacing stimulus is too slow, thus allowing, at regions distal to the pacing electrodes, for the tachycardia to remain. The penetration into the market, or the availability of this form of therapy for patients in need of it, has been severely limited, likely due to its high cost and complexity.

Of the many cases of heart failure diagnosed in the US each year, a significant number of these cases are classified as nonsystolic heart failure. Also known as heart failure (HF) with preserved ejection fraction (EF), these patients have preserved systolic function (e.g., an EF≥50%). The prevalence of this disease is increasing and often affects older individuals, females, the obese, those with hypertension, and those with left ventricular hypertrophy. Despite previous evidence showing that patients exhibiting preserved ejection fraction may have fewer problems than those with a depressed EF, it is believed that patients with preserved EF exhibit substantial mortality rates. It is believed that preserved EF patients were also shown to be at risk for other problems including many of the symptoms of patients with a depressed EF.

This document describes, among other things, devices and methods for overcoming the above-mentioned challenges and others. The present subject matter is exemplified in a variety of implementations and applications, many of which can involve tools and methods that can be helpful, or particularly suited, for certain cardiac conditions advantaged by ventricular pacing. This document includes, among other things, description of systems, devices and methods involving cardiac monitoring and treatments such as ventricular pacing. More particular aspects of the present subject matter can involve use of a cardiac-rhythm therapy arrangement for improving heart function such as by pacing of a patient's left and right ventricles by providing pacing signals to one or more electrodes residing in the patient's right ventricle. Other examples can relate to treatment of patients exhibiting preserved ejection fraction.

Examples include ventricular pacing of the right and left ventricles from a lead in the right ventricle. Embodiments can be used, among other applications, to facilitate mechanically or electrically synchronous contractions such as for resynchronization or to maintain synchrony (e.g., between left and right ventricles) during ventricular pacing. Specific examples can relate to such pacing for treatment of bradycardia.

In an example, a patient can be treated by directly stimulating the normal physiologic conduction system of the heart to elicit a conduction sequence. The conduction sequence can follow the conduction sequence found in a normal heart, both spatially and temporally. The degree to which the conduction sequence follows that of a normal heart can be affected by the state of the myocites, current composition of the extracellular matrix, magnitude, number and distribution of scar tissue due to infarcts, ischemic areas due to coronary obstructions to cardiac blood flow and the status of the myocardial substrate in general.

Aspects of the present subject matter can build upon the discovery relating to simultaneously or nearly simultaneously (e.g., within 1-20 ms) applying two opposite polarity waveforms (e.g., pulse width between 0.01 to 5 ms) to two electrodes with respect to a reference, which can also be referred to as an XSTIM waveform. It has been discovered that it is possible to not only penetrate the root of the His Bundle and Purkinje system, but also to reach regions of the His beyond/below its bifurcation in the multiple bundles. The penetration of the multiple bundles can generate a relatively normal conduction response through the right ventricle, the left ventricle and the septum. This allows for electrical activation of distal bundles at a point that allows bypassing of many conduction defects of the normal physiologic conduction system of the ventricles.

In Example 1, an apparatus includes a pacing output circuit configured to generate a ventricular pacing signal to deliver to an electrode near the His bundle in a right ventricle of a heart to pace the right and left ventricles and improve synchronization of at least one of the ventricles relative to intrinsic activity, wherein the pacing output circuit optionally includes a first terminal configured to deliver a first signal component, a second terminal configured to deliver a second signal component, and a third terminal configured to deliver a reference signal component, wherein the first and second signal components are provided in opposite polarity from each other with respect to the reference signal component, and are substantially identical in duration and magnitude.

In Example 2, the apparatus of Example 1 optionally includes a pacing lead designed configured to deliver an electrode near the His bundle in a right ventricle of a heart.

In Example 3, the pacing output of any one or more of Examples 1-2 is optionally configured to provide the opposite polarity first and second signal components at least partially overlapping in time.

In Example 4, pacing output circuit of any one or more of Examples 1-3 is optionally configured to recurrently reverse polarity of the first and second signal components.

In Example 5, the apparatus of any one or more of Examples 1-4 optionally includes a cardiac function sensor configured to provide information used to control reversing polarity of the first and second signal components by the pacing output circuit.

In Example 6, the apparatus of any one or more of Examples 1-5 optionally includes an atrial sensing circuit configured to sense atrial heart contractions, a controller circuit configured to determine a paced AV delay and to time the paced AV delay from a sensed atrial heart contraction, wherein the controller circuit optionally includes a temporary mode in which the paced AV delay is set to a value that is specified to provide a reduced cardiac output relative to a cardiac output at maximum dP/dt while the pacing output circuit provides the ventricular pacing signal to deliver to an electrode near the His bundle in a right ventricle of a heart to pace the right and left ventricles and improve synchronization of at least one of the ventricles relative to intrinsic activity.

In Example 7, the paced AV delay of any one or more of Examples 1-6 is optionally set to a value that allows mitral valve closure before completion of a left atrial contraction.

In Example 8, the paced AV delay of any one or more of Examples 1-7 is optionally increased after a period of time specified to allow for the heart to recover at the reduced cardiac output.

In Example 9, the apparatus of any one or more of Examples 1-8 is optionally in combination with a guide catheter configured for pace-mapping in a right ventricle at or near the His bundle.

In Example 10, the guide catheter of any one or more of Examples 1-9 is configured such that, once introduced into the right ventricle, a distal portion of the guide catheter assumes a predetermined shape directs one or more electrodes toward a location at or near the His bundle.

In Example 11, the guide catheter of any one or more of Examples 1-10 is optionally configured to assume, responsive to input, two different shapes, including a relatively straight first shape configured to facilitate advancement through a blood vessel and a relatively curved second shape configured to facilitate placement of a distal electrode at or near the His bundle while the guide catheter extends into the right ventricle from the right atrium.

In Example 12, the apparatus of any one or more of Examples 1-11 is optionally in combination with the pacing lead designed configured to deliver an electrode near the His bundle in a right ventricle of a heart, wherein the pacing lead is flexible and wherein the guide catheter is configured to allow for advancement of the pacing lead to position a distal portion of the pacing lead at or near the His bundle, and wherein a distal portion of the pacing lead comprises a fixation mechanism.

In Example 13, the fixation mechanism of any one or more of Examples 1-12 is optionally configured such that at least two separately addressable electrodes can be placed in direct contact with heart tissue.

In Example 14, the apparatus of any one or more of Examples 1-13 is optionally in combination with a guide thread configured to allow introduction and guiding of a chronic pacing lead to a location near the His bundle in the right ventricle of the heart and a retrieving catheter configured to retrieve the guide thread.

In Example 15, the apparatus of any one or more of Examples 1-14 optionally includes a ventricular heart contraction sensing circuit and a controller circuit coupled to the ventricular heart contraction sensing circuit, the controller circuit configured to use information from the ventricular heart contraction sensing circuit to detect a tachyarrhythmia and, in response to the detected tachyarrhythmia, to control the pacing output circuit to deliver the ventricular pacing signal as an anti-tachyarrhythmia pacing (ATP) pulse to an electrode near the His bundle in a right ventricle of a heart.

In Example 16, the apparatus of any one or more of Examples 1-15 optionally includes a defibrillation shock circuit coupled to the controller circuit, wherein the controller circuit is optionally configured to deliver a defibrillation shock when a plurality of the ATP pulses do not restore the tachyarrhythmia to a non-tachyarrhythmia heart rhythm.

In Example 17, the controller circuit of any one or more of Examples 1-16 is optionally configured for controlling the pacing output circuit for using at least a first electrode in a right ventricle of the heart for delivering energy relative to a reference electrode, generating a pacing signal, responsive to depolarization of an atrium of the heart, including a first signal component and a second signal component having opposite polarity, and transmitting, at a pacing rate sufficient for anti-tachycardia pacing (ATP), said first signal component and said second component to said at least a first electrode and, in response thereto, capturing a contraction of a left ventricle of the heart where the contraction is a more rapid and uniform activation than an right ventricular apex ATP pulse.

In Example 18, the apparatus of any one or more of Examples 1-17 is optionally in combination with a guide catheter configured for pace-mapping in a right ventricle at or near the His bundle.

In Example 19, the apparatus of any one or more of Examples 1-18 optionally includes a cardiac function monitor and a controller circuit coupled to the cardiac function monitor and the pacing output circuit, wherein the controller circuit is optionally configured to determine a desired pacing parameter at least in part by iteratively modifying at least one pacing parameter of the pacing output circuit using information received from the cardiac function monitor.

In Example 20, the apparatus of any one or more of Examples 1-19 optionally includes a cardiac function monitor and a controller circuit coupled to the cardiac function monitor and the pacing output circuit, wherein the controller circuit is optionally configured to determine a desired pacing parameter at least in part using information received from the cardiac function monitor regarding at least one of a pacing output amplitude, a QRS width, an AV delay, a pulse pressure, a movement of the patient, a change in blood pressure per time (dP/dt), intraventricular pressure, or a surrogate end-diastolic pressure from a pulmonary artery or vein during pacing of the heart.

In Example 21, the controller circuit of any one or more of Examples 1-20 is optionally configured to determine the desired pacing parameter at least in part using gradient capture responsiveness information received from the cardiac function monitor.

In Example 22, the apparatus of any one or more of Examples 1-21 optionally includes an atrial heart contraction sensing circuit, a ventricular heart contraction sensing circuit, and a controller circuit coupled to the atrial heart contraction sensing circuit, the ventricular heart contraction sensing circuit, and the pacing output circuit, the controller circuit comprising an atrial tracking mode for controlling the pacing output circuit to deliver paces in response to sensed atrial heart contractions, and wherein the controller circuit is configured to inhibit pacing to sense an underlying ventricular heart rhythm, and to exit the atrial tracking mode when the controller determines that the underlying ventricular heart rhythm is not well correlated to a ventricular heart rhythm obtained during the atrial tracking mode when pacing is enabled.

As previously indicated, the above-discussed aspects and examples are not to be treated as limiting the scope or teachings of the disclosure herein. The skilled artisan would appreciate that, partly based on the various discoveries identified herein, the present invention can be embodied in many ways including but not limited to the above-discussed aspects and examples.

BRIEF DESCRIPTION OF THE DRAWINGS

The present invention may be more completely understood in consideration of a detailed discussion of various example embodiments, described in accordance with the present invention, as presented hereinafter in connection with the following figures, each of which is consistent with the present invention.

Figure 1:
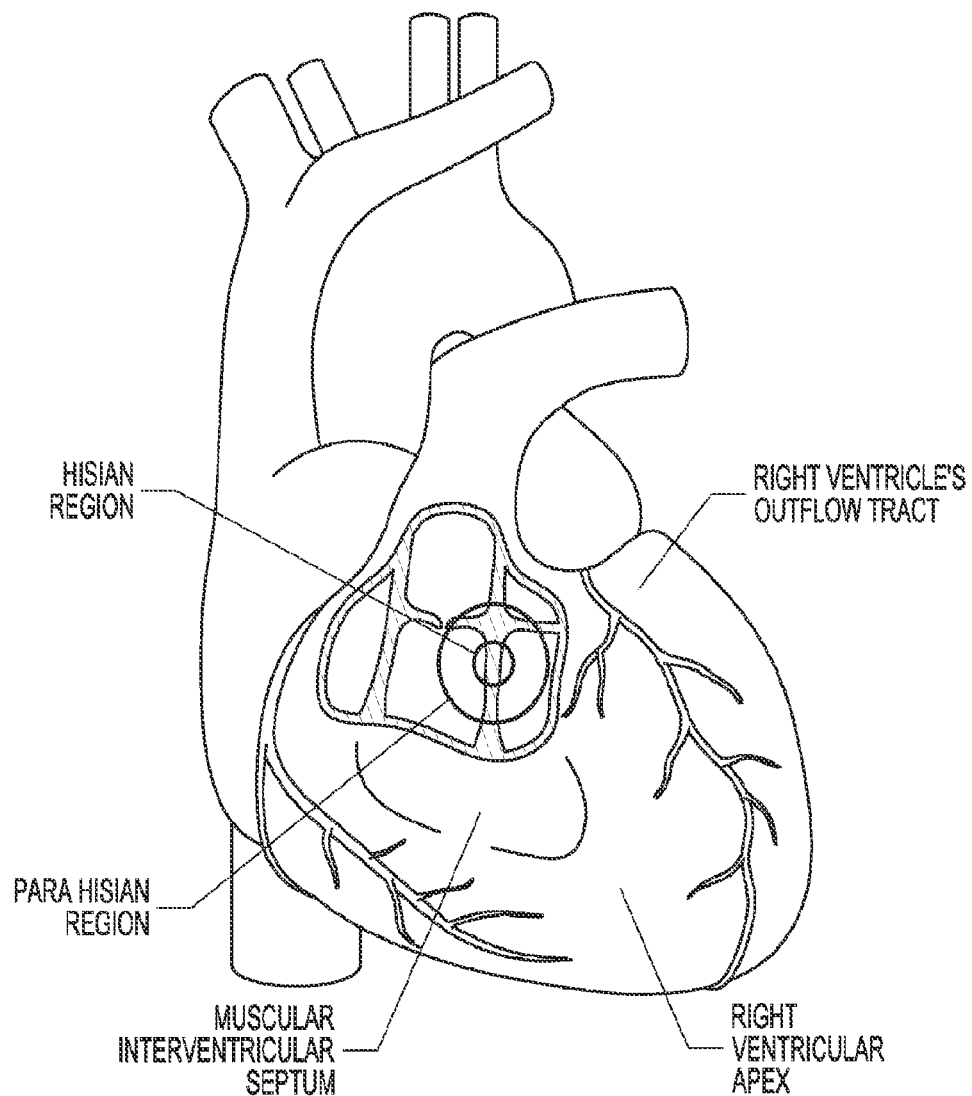
FIG. 1 shows a cross-sectional view of a heart and the Hisian and para-Hisian regions, consistent with an embodiment of the present invention.

While the invention is amenable to various modifications and alternative forms, various embodiments have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present subject matter is believed to be applicable to a variety of different types of devices and approaches, and is believed to be particularly suited for maintaining or re-establishing a normal conduction of the activation sequence of the ventricles. Such conduction can be improved in both its spatial and time distributions. This can be accomplished from a lead introduced in the right ventricle. In an example, the lead can have electrodes positioned behind the root of the septal leaflet of the tricuspid valve. The exact pacing location can depend on the location of the conduction block that needs to be bypassed. This pacing can depend upon the location of the bundle fibers that are interrupting the conduction circuit, thereby creating an abnormality. In many patients this location can be close to the septal leaflet of the tricuspid valve and the fibrous atrio-ventricular and interventricular septum. While the present subject matter is not necessarily limited to such applications, various aspects of the subject matter can be appreciated through a discussion of various examples using this context.

The present inventors have recognized, among other things, that various methods and devices can help facilitate the deep penetration of electrostimulation into the His root and distal Bundles. This penetration can include the left bundle and its bifurcations, the right bundle and its bifurcations, and the septal bundle. This can be particularly useful for electrically bypassing various types of bundle branch blocks (e.g., right bundle branch block RBBB, proximal and distal; left bundle branch block LBBB, proximal and distal; left anterior hemiblock LAHB, proximal and distal, left posterior hemiblock LPHB, proximal and distal, intraventricular conduction defects IVCD, RBBB with left axis deviations and many other kinds of complex conduction defects). In an example, the present subject matter can be directed to the ability and use of a waveform, such as XSTIM, to penetrate deeply into the conduction system near the His Bundle. For example, it is believed that using an XSTIM waveform can create a larger virtual electrode than with other waveforms and can be useful to overcome capacitance of the body.

The conduction system near the His Bundle can be thought of as a group of multiple electrical conductors each surrounded by electrical isolators. Thus, pacing signals introduced to the conduction system can be affected by capacitance between the electrical conductors. The electrical conductors are able to conduct the electrical impulse longitudinally from cell to cell of the electrical conductor, but there is very little conductivity, within the bundles, in the transversal direction. However, it is believed that strategically located bridges between cells allow the electrical stimulus to jump from one bundle to the other. This mechanism is believed to provide some redundancy in case a particular bundle stops working, for instance due to an infarct or micro-infarct. The bundles branch into sets of multiple conduction fibers as they progress towards their destination at the Purkinje fibers. The sets of fibers are electrically isolated from the rest of the myocardium by specialized tissue to prevent electrical depolarization of the surrounding myocites from electrical pulses passing through the specialized conduction system. It is believed that this combination of electrical conductors and isolators effectively creates a distributed capacitor network, with, in its transversal cut, the bundle of His being in the middle of at least two serial capacitors. Because the cell membranes of the His bundle cells are also isolators, the intracellular fluid inside the His bundle cells is placed inside still another capacitor.

The XSTIM waveform provides a relatively large virtual electrode, whose asymmetrical dog bone shape will be affected by the polarity of the waveform, henceforth allowing the penetration of the waveform to be adjusted by modifying the relative polarities applied to the two electrodes. The XSTIM waveform also provides a high frequency stimulation energy that is able to bypass the capacitors. Thus, it is believed that the XSTIM waveform is able to deeply penetrate the His bundle. When using the XSTIM waveform's two opposite polarity pulses, the pulses can be provided such that the pulses overlap in time (completely or partially). Such pulses need not have any overlap. For example, the pulses can also be separated by a few milliseconds (e.g., 0 to 20 ms). Thus, the waveform can be selected between a variety of different configurations so as to help penetrate and reach the fibers, even distal fibers, otherwise thought to be unreachable.

Furthermore, it has been discovered through experimental data that there is not a single capture threshold for the myocardium and for the His bundle. Indeed the response in many patients varies as the pacing voltage is increased. When the XSTIM amplitude is gradually increased from subthreshold values, a first capture threshold is found that triggers a depolarization sequence that activates the ventricles. This depolarization sequence often uses a significant amount of cell-to-cell conduction of myocardial tissue. In many patients a second pacing threshold exists where some (or additional) fibers of the His bundle are captured. It is believed that often this second pacing threshold does not reach or capture all of the His bundle. For instance, in patients with ventricular conductions defects, a continuous change in the electrocardiogram (ECG), QRS width, level of fractionation, and vector of the 12 lead ECG has been observed when the XSTIM pacing amplitude is further increased. Eventually, a saturation point is reached and little or no further improvement is seen. It is believed that through careful positioning and selection of amplitude level, the pacing stimulus is able to reach the furthest blocked fibers of the conduction system, thus improving the coordination of the contraction to near normal levels.

The ability to achieve a normal conduction response may depend on the health of the substrate including, but not limited to, number of infarcts, myocites degeneration, availability of mitochondria, blood supply, presence of interstitial fibrosis, degradation of the metallo-proteinase matrix, etc. The implication of these and other findings is that a similar effect can be achieved with a variety of wave-shapes and electrode configurations designed to traverse the capacitive networks (e.g., due to high frequency signal components). The effective capacitance is lower for higher frequency components, including frequency components that are sufficient to trigger an action potential (0.01 to 20 ms). While some waveforms may be less efficient and use more energy to achieve similar results, the present subject matter is not limited to applications of the most efficient waveforms.

A particular embodiment of the present subject matter relates to bypassing conduction defects to improve heart function and Heart Failure in patients with preserved Ejection Fraction and ventricular conduction defects. Human study data has shown that His pacing improved hemodynamic response of heart failure patients with preserved EF. This pacing was conducted using an XSTIM waveform. It is believed that these patients may benefit from physiologic heart rate response.

In one embodiment, rate responsive pacing for the atrium is combined with His pacing in the ventricle, XSTIM or otherwise.

Another embodiment of the present subject matter relates to therapy using an electrical stimulus that electrically bypasses conduction defects near the root of the His bundle in patients with conduction defects and preserved ejection fraction heart failure.

Among all the patients who are hospitalized for Heart Failure, there are around 50% of the total that, despite their heart failure, have a preserved ejection fraction. This means that the fraction of the total ventricular volume ejected with each beat is not as seriously depressed as it is in their counterparts. These patients are thought to have diastolic dysfunction in contrast with the heart failure patients with depressed ejection fraction, who are thought to have a depressed systolic function. Different intraventricular conduction defects are common in both groups of patients.

It was discovered that the electrically bypassing of these conduction defects was possible in either group of patients (e.g., when electrically stimulating at or near the region of the His bundle). This discovery is particularly surprising because such conduction defects were taught to be distal to the His bundle and because it was also taught that only defects of the proximal His bundle could be bypassed with His stimulation. Moreover, for the group of patients with diastolic dysfunction, it was discovered that their systolic function could be improved even where the ventricular conduction defects could be bypassed. Such a discovery is surprising because the defect was previously believed to be in the diastolic function and not in the systolic function.

It has been discovered that by bypassing these ventricular conduction defects with XSTIM or with other waveforms capable of penetrating deep enough in the region of the root of the His Bundle (electrical bypass pacing or EBP), not only is it possible to improve diastolic function but also systolic function in the patients with Heart Failure (HF) and preserved Ejection Fraction (EF).

Embodiments of the present subject matter can leverage from the abovementioned discoveries. In an embodiment, an atrioventricular pacemaker is implemented. The pacemaker uses near His Electrical Bypass pacing (EBP) and can be particularly useful in improving both diastolic and systolic function in preserved EF HF patients. In an implementation, mechanical synchrony can be maintained between the atrial contraction and the ventricular contraction by sensing the atrial activity, either from the lead and electrodes used for near His root pacing or from the same lead with different electrodes or from another specific lead placed in the atrium for atrial activity sensing. Ventricular pacing for EB can then be triggered after a brief AV delay that allows the electrical conduction to propagate from the sinus node to the Hisian side of the AV node. This AV delay can be calculated by measuring the AH (Atrio-Hisian) interval and programming the AV delay. In an example implementation, the AH delay can be on the order of about 10 milliseconds (ms).

FIG. 1 shows an example of a cross-sectional view of a heart and the Hisian and para-Hisian regions. In particular, FIG. 1 is an example of a view of the right side of the heart, with the Hisian and para-Hisian pacing areas shown by the dotted lines. These regions represent the general area in which the pacing sites for the experimental data were collected.

Figure 2:
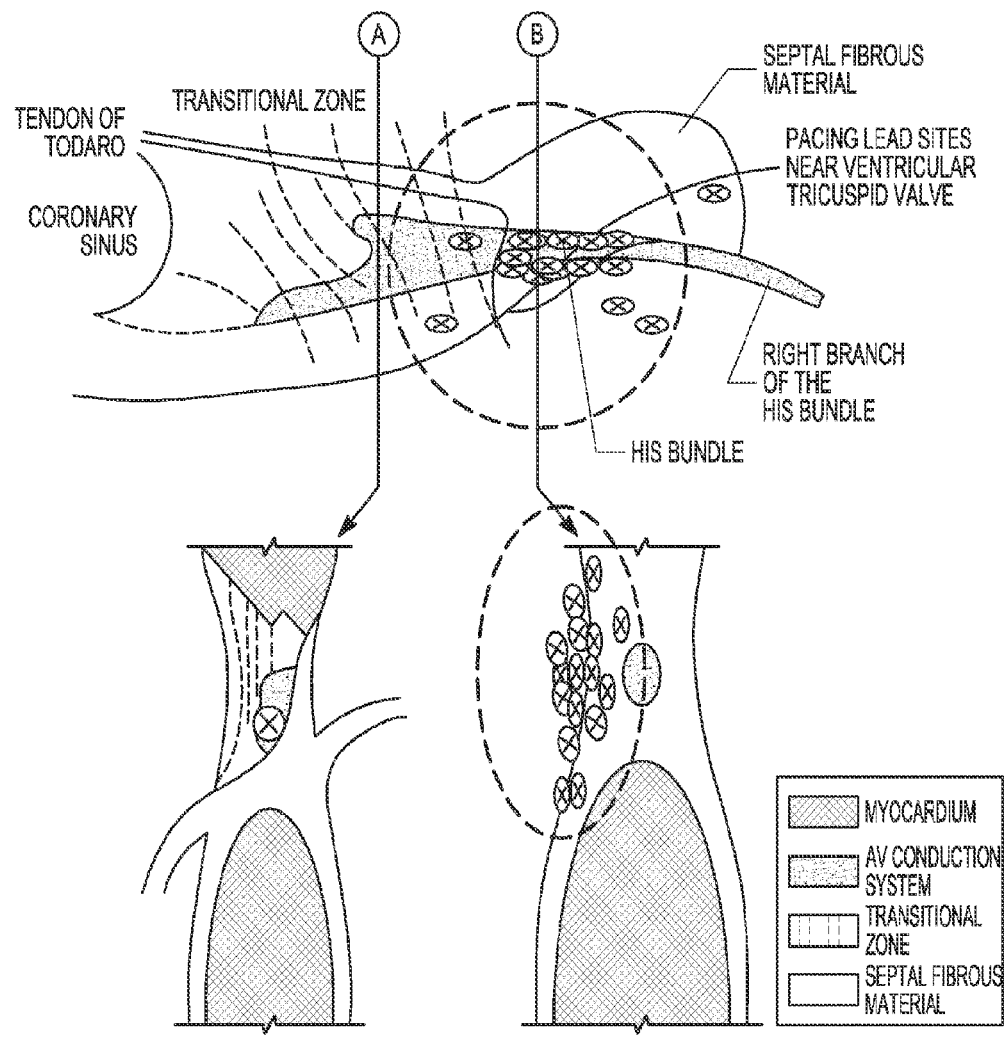
FIG. 2 shows pacing site locations on cross-sectional views of the heart, consistent with an embodiment of the present invention.

FIG. 2 shows an example of the location of pacing sites on several cross-sectional views of the heart. The upper view is an example of a sectional view that includes part of the conduction system that includes the AV node, the His bundle and the right bundle branch. The lower two views show respective perpendicular views taken at respective portions of the conduction system of the upper view.

Figure 3:
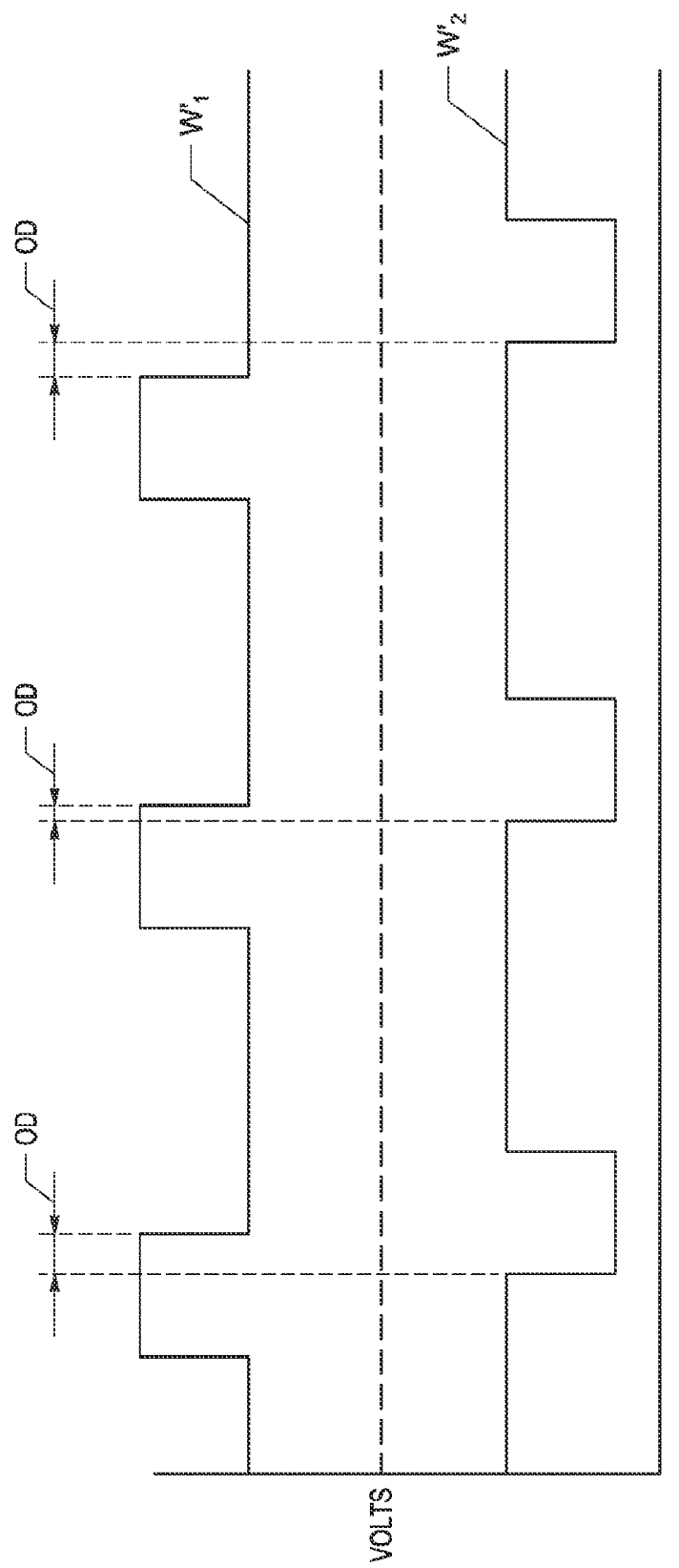
FIG. 3 shows pacing waveforms, consistent with an embodiment of the present invention.

In an example of the present subject matter, a pulse generator can be configured to generate an XSTIM waveform, which comprises a first and a second pulsed waveform $W_1$, $W_2$ applied, respectively, to first and second electrodes. FIG. 3 shows an example of such waveforms $W_1$, $W_2$, consistent with signals generated by such a pulse generator. By way of example, and not intended to be limiting, the pulse duration (PD) can be between about 0.1 to 2.0 milliseconds, the amplitude A can be 0.1 Volts to 10 or 20 Volts and the time delay TD between pulses can correspond to a targeted heart rate (e.g., 50 to 200 beats per minute).

The pulses are shown as square waveforms but, in practice, can be any of various geometries. In FIG. 3, the first electrode can provide positively charged pulses only. The second electrode can provide negatively charged pulses only, which can be timed to coincide with the positively charged pulses of the positive electrode. While direct current (DC) pulses are shown, the electrodes could be energized with alternating current pulses with the signals to the electrodes being out of phase, such that the positive pulses on the first electrode coincide with negative pulses on the second electrode and negative pulses on the first electrode coincide with positive pulses on the second electrode.

Waveforms $W_1$, $W_2$ can be provided simultaneously or out of phase with one another. The first set of pulses illustrated in waveforms $W_1$, $W_2$ present a partial overlap duration (OD). In this first set of pulses OD is a positive value. Although not shown, this overlap can also be a complete overlap, when OD is a positive value equal to the entire duration of the pulses. The second set of pulses are further out of phase such that the beginning of one pulse coincides with the end of another pulse (OD=0). The third set of pulses includes pulses that are out of phase such that the leading edge of one pulse occurs after the end of the first pulse of the set (OD has a negative value).

Thus, for various implementations at least a portion of time can include a monopolar pacing between one of the electrodes and the reference electrode. This pacing creates out-of-phase monopolar fields. Values of OD can range from the entire pulse length (e.g., around two milliseconds) to a negative value of several milliseconds (e.g., around negative two milliseconds). Although not explicitly shown in FIG. 3, either of the negative or positive pulses can lead the other pulse, respectively. Also, while the magnitudes of the two waveforms are shown to be equal, they need not be equal in practice nor do they necessarily need to be implemented as strict square waves. For non-square wave pulses or pulses with relatively slow fall or rise times, the OD can be calculated accordingly. In one example, the OD may be calculated from beginning or end of the rise/fall of each pulse, respectively. In another example, the OD may be calculated from when each pulse reaches a certain voltage level, respectively, or once the pulse has maintained a certain voltage level for a period of time.

The present inventors have recognized that, among other things, the pacing threshold can change over time. Without being bound by theory, there are a number of potential sources for such threshold changes, some of which will be discussed hereafter.

Electrical stimulation can be produced by alternating ionic flows triggered by changing the electrical potential applied to an (e.g., metallic) electrode. This voltage application can produce both reversible and non-reversible electrochemical reactions within the heart. The efficiency of such electrochemical reactions can depend upon the availability of ionic species required for the reactions to take place. Bypassing distal blocks of the His bundle can be facilitated by using certain stimulation waveforms, configurations and shapes. In particular, the stimulation waveform can be selected so as to provide sufficient penetration into the distal fibers of the bundle to be able to affect the electrical bypass. In a particular implementation a relatively high-level of current can be provided at a stimulation site that has been identified, such as with pace mapping of the region of the His bundle near the septal side of the septal leaflet of the tricuspid valve.

A problem that can be associated with high penetration stimulus is that too many reactants can be used to create an efficient transfer of energy from the metal to the electrolytic fluid present in the interface and the interstitial fluid. It is believed that this can exhaust the reactions, with the consequent phenomenon of an apparent increased capture threshold (e.g., failure to achieve the same pacing-effectiveness at the same voltage). In the case of the electrical bypass, an apparent increased capture threshold can signify that the distal fibers are not being stimulated. It is believed that this can result in progressively decreasing the efficiency of the electrical bypass as the farther fibers drop from the field of influence of the waveform and waveform configuration being used.

Another potential issue is the property of a nerve to adjust to a slowly increasing pacing waveform, so that its threshold of excitation is greater than had the pacing waveform exhibited a more rapid increase in strength or voltage. This effect is sometimes referred to as accommodation of a nerve. Without being bound by theory, such an accommodation effect may play a role in increasing the pacing threshold. For instance, the intrinsic capacitance of the body may both reduce the effective rate of stimulus increase for a waveform and create an effective voltage residual stored by the capacitance. Thus, the effective change in voltage can be reduced with respect to rate (dV/dt) and/or with respect to effective change in voltage (e.g., due to residual voltage).

This effect can be minimized by alternating the polarity or current flow direction. For instance, it is believed that different types of reactants are used relative to the stimulus polarity for a pacing cycle. Accordingly, alternating the polarity or current flow can be useful for allowing time for those reactants to be replenished. An added benefit of this type of stimulation is that there is no net current flow between the electrodes when two pacing cycles are considered. This can help reduce or eliminate plating or metal deposition effects that could otherwise occur, such as when a net current is applied. Compounding the problem, the current can be present even between pacing stimuli, such as due to leakage current of the pacing device (e.g., due to capacitive leakage). This can be particularly problematic for a device that will be pacing for many years using the same electrode.

In an example, the first pacing pulse can be sent with the positive of the output of the pulse generator connected to the tip of the pacing catheter and the negative of the output of the pulse generator to the ring of the pacing catheter, the second pacing pulse can be sent with the negative of the output of the pulse generator connected to the tip of the pacing catheter and the positive of the output of the pulse generator to the ring of the pacing catheter, the third pacing pulse can be sent with the positive of the output of the pulse generator connected to the tip of the pacing catheter and the negative of the output of the pulse generator to the ring of the pacing catheter and so on and so forth, alternating polarities with every pacing stimulus sent to the heart.

In an example, at least one of the electrodes can be located a significant distance from the pacing site. For instance, the pacing pulses can be sent between the tip of the pacing catheter and the can of the pulse generator. The polarities between these points can be reversed, as desired, such as in an alternating fashion. In another instance, the pacing pulses can be sent between the tip of the pacing catheter and another electrode located on another lead. The other lead can be placed within the heart or at another location of the body.

In an example, the alternation in polarity can be periodic. For instance, the polarity can alternate every N beats, where N can be specified as 2 or more beats. The value for N can be set by a physician or by the device manufacturer. In an example, N can be a certain time period rather than a number of beats.

In an example, the polarity can be alternated after N beats/time and alternated again after M beats/time. For instance, a particular polarity can be considered the preferred polarity. Thus, where N represents the preferred polarity, N can be greater than M, thereby using the preferred polarity for the majority of the time. In a particular instance, M can be equal to one beat, or to a similarly small amount of time. Thus, the polarity can still be reversed, but only for a relatively short period of time, in an example.

In an example, the alternation of polarity can be responsive to a sensor or other input. For instance, a partial or complete lack of pacing capture can be detected by a sensor, and used to trigger a change in the pacing waveform. In an example, the change in the pacing waveform can include a change in the polarity of the waveform. Other waveform changes can also be implemented including, but not limited to, stimulus strength, stimulus duration and waveform morphology. These changes in the pacing waveform can be implemented independently from one another or in various combinations.

In an example, the waveform used can be a bipolar waveform. During the first beat the positive phase can be applied first to the more proximal ring electrode and in the second beat the positive phase can be applied first to the more distal tip electrode. The examples discussed herein can also be implemented with a monophasic or a biphasic waveform.

The present inventors have also recognized, among other things, that resynchronization therapies using biventricular pacing are not generally optimized for preload of the ventricles of the heart independently from the contraction synchrony of the heart. For example, the object of such therapies is to activate the largest possible area of the heart at nearly the same time. This generally involves pacing that is determined by when the three activation wave fronts collide in time and space at the optimum place. Since this optimum collision depends on three activation wave fronts: 1) from the pacing spike in the right ventricular lead; 2) from the pacing spike of the left ventricular lead; and 3) from the normally conducted activation that comes from the AV node (e.g., in non-AF and non-$3^{rd}$ degree AV block patients that are the majority), this optimum collision can be significantly affected by the choice of the AV delay. Thus, optimizing preload by selecting the AV delay affects the synchronicity and vice versa.

Using His electrical bypass, synchrony of the contraction can be achieved at essentially all AV delays that are shorter than or equal to the intrinsic AV delay. Such synchronization does not depend on the optimal collision of wave fronts coming from different points that are being excited at physically different places in the ventricles. This allows the practitioner to optimize preload independently of synchrony.

In heart failure patients, the heart can often be very sick. In such instances, reducing the load of the heart can be desirable to allow the heart to recover. For example, reducing the load of the heart can allow for recovery of the heart by halting or even reversing the degenerative processes associated with heart failure. This reduction in load can also be used to treat the maladaptive mechanisms (e.g., dilatation)—even allowing for reversal of the maladaptive mechanism. Accordingly, for a very sick heart the AV delay can be tailored to reduce the load of the heart, to allow for its recovery, rather than to maximize the cardiac output that the heart can provide to allow the body to maximize its exercise capacity (e.g., AV delay optimization for maximization of cardiac output or dP/dtmax).

Aspects of the present subject matter can be useful for reducing the AV delay (thereby reducing preload) while maintaining the synchrony of the contraction of the left and right ventricles. This synchrony can help to reduce maximum stresses in the late-activated regions of the heart. It is believed that these stresses can be a significant cause for many maladaptive compensatory processes, like dilatation. Accordingly, the curative process is expected to result from improvement in the synchronicity of contraction. By also setting the AV delay to a small value, the stress on the heart can be improved upon relative to synchronicity alone.

In an example, the intrinsic AV delay can be determined by echocardiography. The paced AV delay can be set relative to the end of the left atrial contraction and the associated closing of the mitral valve. For example, the paced AV delay can be set to the shortest possible value that doesn't allow the mitral valve to close before the left atrial contraction ends. This short-AV delay can then be maintained by the device for a specified period of time such as to allow for recovery by the sick heart. For instance, the short-AV delay can be implemented for a number of weeks, as determined by a physician. The amount of time can vary, such as depending on patient condition and estimated time of recovery of the heart. In an example, this short-AV delay time-period can range from 2 to 50 weeks such as depending upon the severity of one or more indications. After the time-period ends, the AV delay can then be increased, thereby increasing the cardiac output (e.g., dP/dt). In an example, the AV delay can be progressively increased (e.g., by 1-100 ms per week). This can be an automatic increase built into the device and can continue, such as until the optimum preload for a recovered heart is reached. In an example, the optimum preload can be defined as the preload that maximizes exercise capacity or maximizes cardiac output.

In an example, a device can be programmed with an initial, short delay and a longer AV delay target. The AV delay target can be eventually obtained by slowly increasing the AV delay from the short value to the long value. In an example, the time period necessary to reach the AV delay target can be determined by a physician (e.g., using clinical judgment).

In an example, the measurements can be easily done using Doppler echocardiography. Optimizing the AV delay in this manner can allow the heart to work with a low preload, such as to increase the likelihood of reverse remodeling. After the heart shows improvement or reverse-remodels, the AV delay can then be increased to a setting that can be set using one or more techniques (e.g., ECG, RV pressure, LV dP/dt, ECG measurements, LVEDP, etc.).

The present inventors have also recognized, among other things, that aspects of the present subject matter can facilitate positioning of a pacing catheter near the root of the His bundle. The guide catheter can allow for implantation through the Superior Vena Cava. The guide catheter can have a semi-rigid pre-shaped design, such that once inserted into the right ventricle, an electrode can be directed near the posterior aspect of the septal leaflet of the tricuspid valve in the right ventricle, such as right behind the annulus that supports the valve.

In an example, the guide catheter can be introduced with a guiding wire that can straighten the pre-shaped portion, such as to allow for introduction into the right ventricle. Once the guiding catheter has been positioned inside the right ventricle, the guide wire can be slowly removed. The removal of the guide wire can allow the guide catheter to assume the pre-shaped form. In an example, the guide catheter can transition from a relatively straight configuration, pointing toward the apex of the ventricle, to a curved configuration. Further removal of the guidewire and further push on the guiding catheter can make the catheter pivot on the right ventricular apex and advance retrogradedly back on itself toward the septal leaflet of the tricuspid valve. The guidewire can then be removed and the guiding catheter pushed in, such as until the tip of the guiding catheter is located between the septal leaflet of the tricuspid valve and the interventricular septum. At this point the electrode that is at (or near) the tip of the guiding catheter can be used to pace map, such as to locate the exact site at which the electrical bypass of the distal His conduction block can be best accomplished. In an example, the tip electrode of the permanent positive fixation pacing catheter can be used for this pace mapping. Once the optimum site is located (e.g., using the systolic pressure of the patient, using the QRS width of the 12 lead electrocardiograms or at a single lead electrocardiogram, or using the vector direction represented by the electrocardiogram), the implantable pacing catheter can be introduced through a lumen in the guiding catheter, such as until the tip touches the septal wall or the annulus of the tricuspid valve at the optimum site. The pacing catheter can then be attached (e.g., screwed-in such as by using exposed screw-in catheter or a retractable screw-in catheter) at the optimum site. The procedure can then include extracting the guiding catheter and leaving the pacing catheter in place. This last step can be accomplished by a number of methods including, but not limited to, the following three methods: 1) using a connector at the end of the pacing catheter that fits into the lumen of the guiding catheter and then pulling the guiding catheter out slowly and carefully so as not to detach the screwed in pacing lead; 2) similar to method (1) but while holding the pacing catheter with a long (e.g., 2× length of pacing lead) holding wire; and/or 3) by marking the guiding catheter with a cut that allows the peel-away of the guiding catheter as it is pulled out by cutting itself in half when the physician extracting it holds a special tool that finishes the factory pre-cut.

Figure 4:
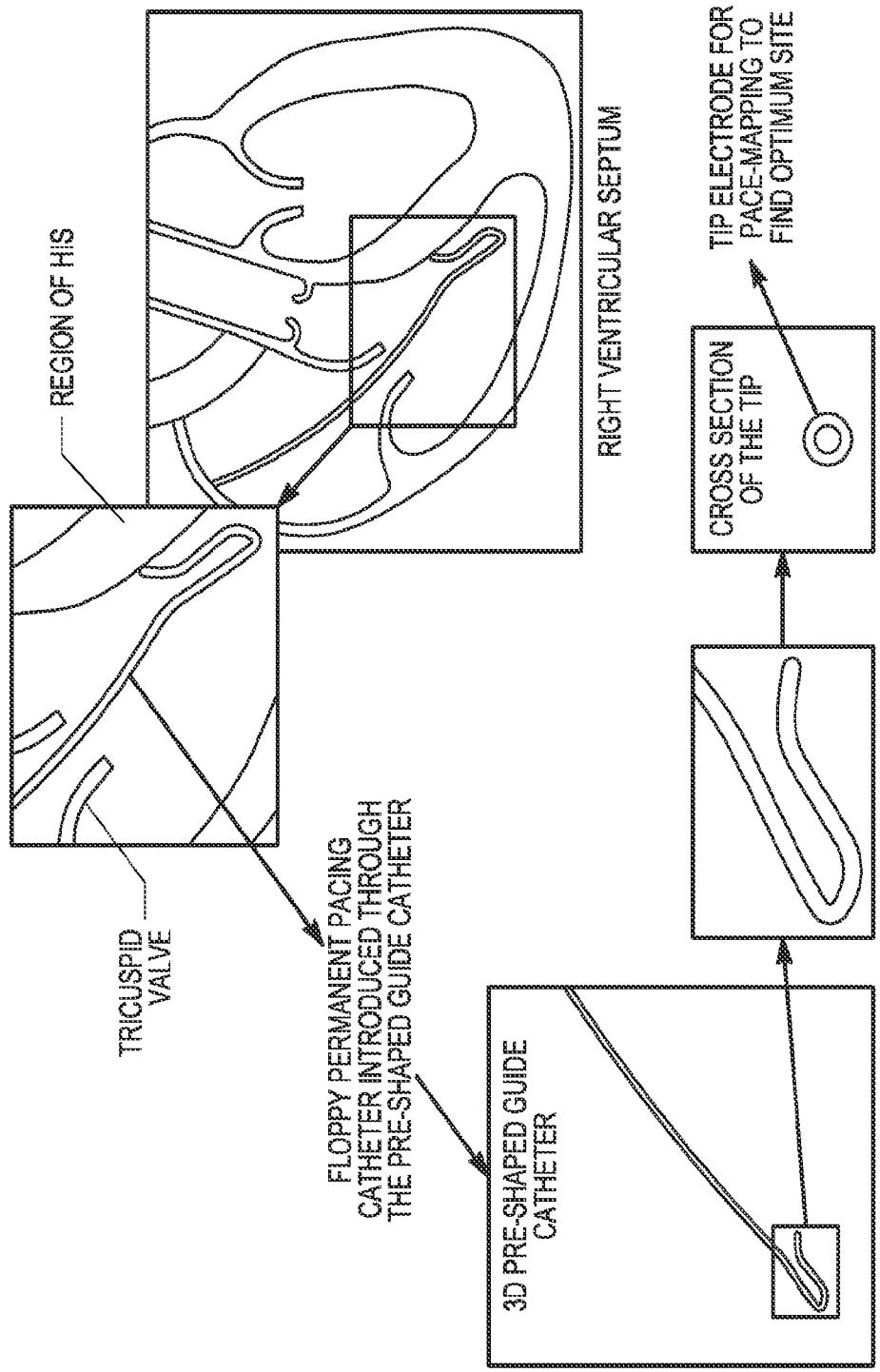
FIG. 4 shows a guide catheter consistent with an example embodiment of the present invention.

FIG. 4 shows an example of a guide catheter, consistent with an example of the present subject matter. The guide catheter can facilitate pace mapping and subsequent placement of a relatively-permanent pacing lead. This guide catheter can include a series of bends that can allow the guide catheter to enter the ventricle at an angle that can be substantially vertical relative to the septal wall while simultaneously presenting one or more pacing electrodes to the septal wall near the His bundle.

The present inventors have also recognized, among other things, that certain aspects of the present subject matter can relate to anti-tachycardia. The present inventors have recognized that by pacing near the root of the His bundle (e.g., with XSTIM or other waveforms that allow penetration of the bundle including distal fibers) can bypass distal bundle blocks and even diffuse blocks. This discovery enables use of the normal conduction system to activate ventricles that have conduction defects previously believed to necessitate apex-based pacing. The present inventors have recognized, among other things, that this new form of pacing can also be applicable to anti-tachycardia pacing (ATP), offering the advantage of much faster propagation times due to its ability to electrically bypass conduction blocks—even blocks that are supposed to be distal to the left bundle branch of the His system. It is believed that this faster propagation time can be particularly useful for achieving a higher success rate for anti-tachycardia pacing by facilitating delivery of the pacing stimulus to the heart using the normal conduction system. Generally speaking, the conduction system delivers pacing signals much faster than the cell-to-cell conduction that would be otherwise obtained, such as from an apex location.

Embodiments of the present subject matter can include a device that includes a defibrillation backup, such as to ATP, as well as a device that need not include a defibrillation backup. This allows for the use of cheaper devices such as for patients that do not require the presence of a defibrillation shock backup. According to an example of the present subject matter, this form of therapy can provide therapy to revert tachycardia episodes.

Figure 5:
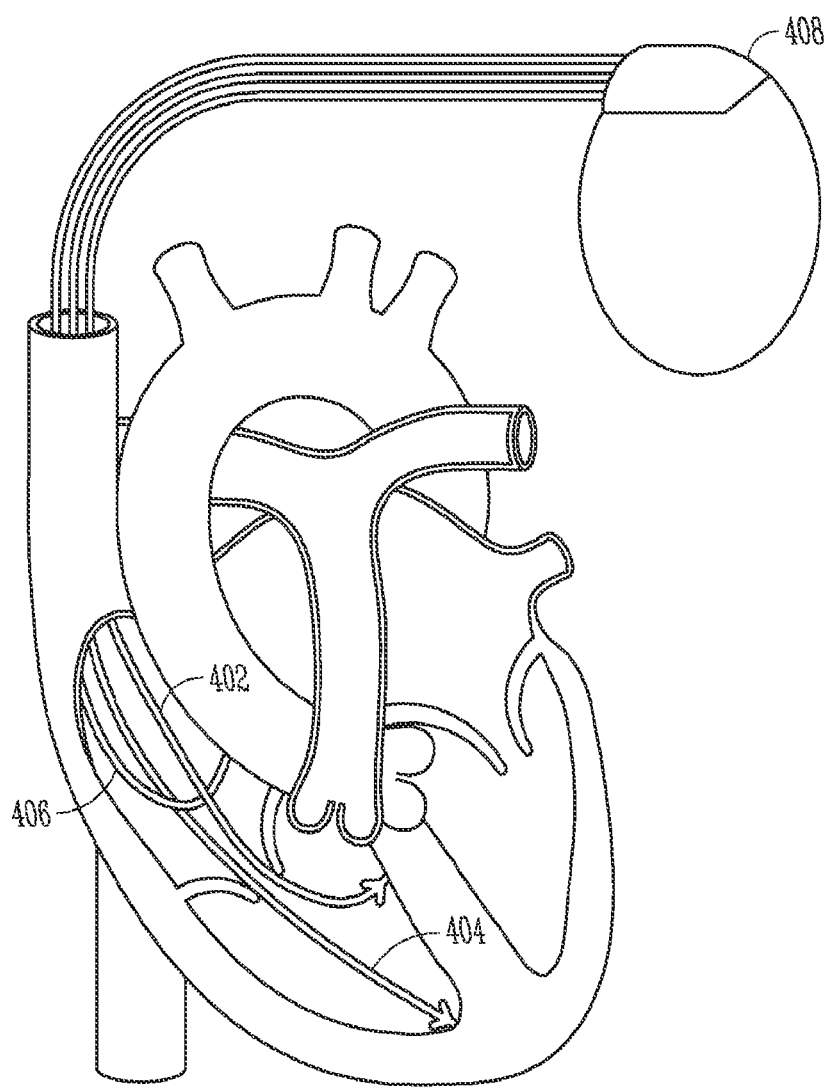
FIG. 5 shows an example device for pacing, consistent with various embodiments of the present invention.

FIG. 5 shows an example of a device for pacing, consistent with various embodiments of the present subject matter. In an example, a signal generator unit can provide various signal components such as to leads 402, 404 and/or 406. Lead 402 can be designed and placed to allow for electrical bypassing of conduction defects and/or allow for use of the heart's natural conduction system. Optional leads 404 and/or 406 can be used for various purposes. For instance, lead 404 can be used to provide defibrillation and lead 406 can be used for pacing and/or sensing in the atrium.

Figure 6:
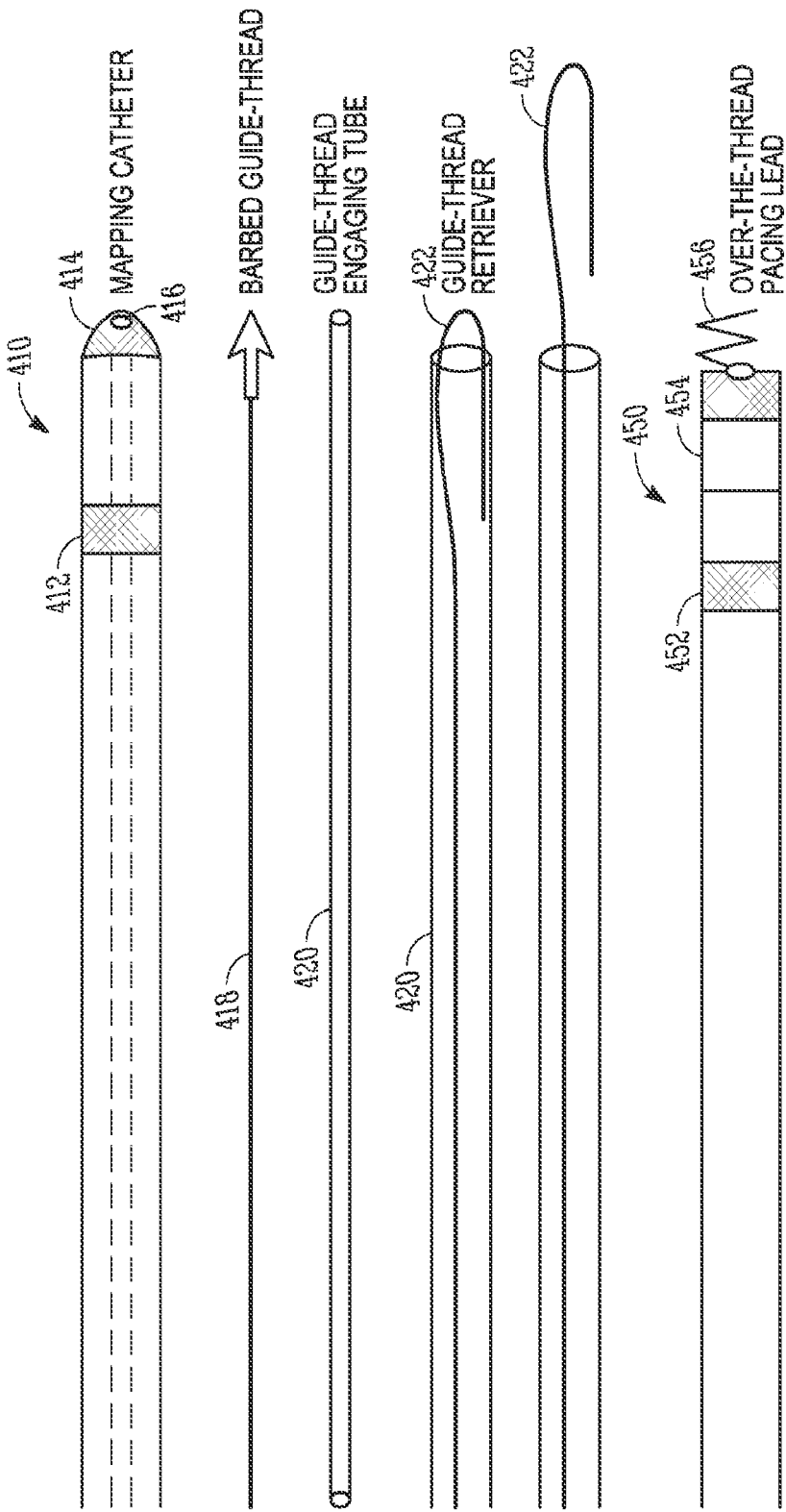
FIG. 6 depicts an example catheter for IVC-based pacing implantation, consistent with an embodiment of the present invention.

Aspects of the present subject matter can relate to the use of methods and devices that involve introduction of a pacing catheter through the inferior vena cava (IVC). Access to the IVC can be obtained through the groin (e.g., via the femoral vein). FIG. 6 depicts an example of a catheter such as for IVC-based pacing implantation. A mapping catheter 410 can be advanced through the IVC and into the right side of the heart. The mapping catheter 410 can include one or more electrodes 412, 414 such as for delivering pacing components to the heart. Upon determining the target pacing location, lumen 416 can be used to advance barbed guide-thread 418 such as for affixation to the target location. Mapping catheter 410 can be subsequently removed.

A guide thread retriever device 420, 422 can be used to retrieve the guide thread. This can be particularly useful for the introduction of the more-permanent pacing lead such as by using a different entry point, e.g., using subclavian vein catheterization (SVC). In an example, lumen 420 guides a retrieval hook 422 near the guide thread. Retrieval hook 422 allows for the guide-thread to be retrieved through the different entry point. Thereafter, the guide-thread retriever device 420, 422 can be removed.

The over-the-thread pacing lead 450 can then be introduced to the pacing location such as by using the retrieved guide-thread 418. Over-the-thread pacing lead 450 can include one or more pacing electrodes 452 and 454. A fixation mechanism 456 can be used to attach the pacing lead to the heart tissue at the target pacing location.

Figure 7:
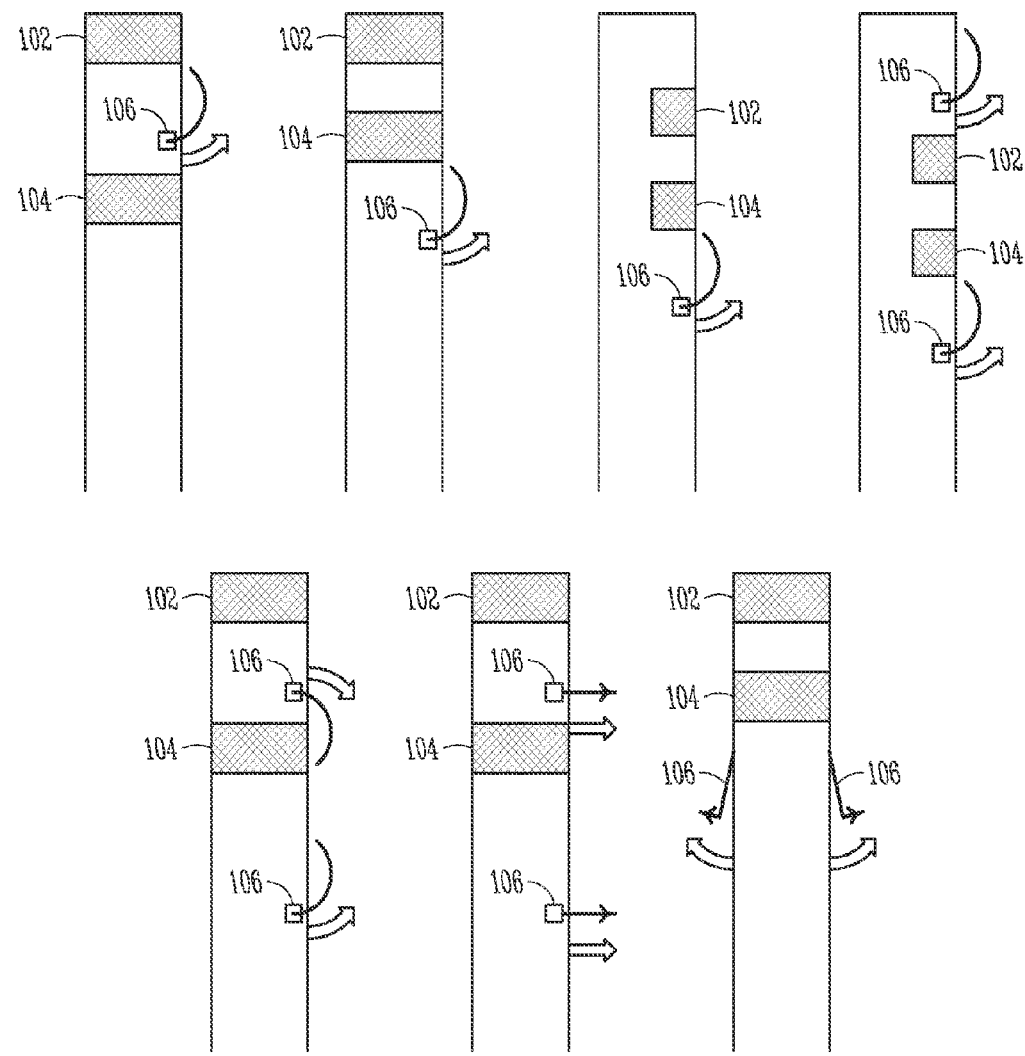
FIG. 7 shows example pacing leads, consistent with embodiments of the present invention.

Aspects of the present subject matter can relate to pacing leads and their attachment mechanisms. Examples of such pacing leads are depicted in FIG. 7. In an example, the pacing lead can have one or more electrodes (102, 104) used to deliver pacing components. It can be desirable for these electrodes to have direct physical contact with the heart tissue. For instance, direct physical contact with the heart tissue can help create a low-impedance electrical connection between the electrode and the heart tissue. Other factors that can be affected by direct contact include, but are not limited to, signal reflections and penetration depth of the electrical stimulus. It can also be desirable for the location of the pacing electrodes to be easily manipulated prior to fixation to the heart. For instance, aspects of the present subject matter can be used with various pace-mapping approaches such as to determine a target pacing location. The electrodes 102, 104 can be implemented in a variety of different orientations and shapes. In an example, the electrodes 102, 104 can be located on the exterior of the longitudinal portion of the pacing lead. The electrodes 102, 104 can circumscribe the pacing lead or be located on substantially the same side of the pacing lead, such as to allow for both pacing leads to be in direct contact with the heart tissue at the same time.

In an example, a fixation mechanism 106 can secure the pacing lead to the heart tissue. In an example, the fixation mechanism 106 can include one or more tines or helixes that can be embedded into the heart tissue. The orientation and location of the fixation mechanism 106 can be selected to ensure that once the pacing lead is affixed to the heart tissue the electrodes 102, 104 can be in physical contact with the heart tissue. A number of different electrode and fixation locations are shown in FIG. 7. It should be apparent that these are merely examples and that a variety of other combinations and configurations are possible. For instance, there can be more than two fixation tines. In another instance, the fixation mechanism 106 can take one or more different forms including, but not limited to, barbs.

In an example, the fixation mechanism 106 can be contained (partially or wholly) within the catheter body until fixation is desired. Once fixation is desired, the fixation mechanism 106 can be extended through a passageway and into the heart tissue. The arrows next to the various depictions of fixation mechanism 106 show example movement directions for penetration into the heart tissue (e.g., wall of the septum). The extension can be triggered by rotating or pushing a component of the catheter that triggers the extension. This configuration can facilitate pace mapping using the catheter, which can be followed by selective extension of the fixation mechanisms.

Various other configurations are also possible, including spring-loaded fixation mechanisms. In an example, the fixation mechanism 106 need not be located within the catheter during placement and then extended through a passageway upon fixation. For instance, the fixation mechanism could be located on the exterior of the pacing catheter in a manner that does not significantly impede movement of the catheter along the wall of the septum. Once the desired location is achieved, the fixation mechanism 106 can be triggered (e.g., extended, expanded or otherwise modified) so as to fix the catheter in a more permanent manner. This includes, for example, fixation mechanisms located in one or more recesses so as not to impede movement of the catheter during pace mapping.

Figure 8:
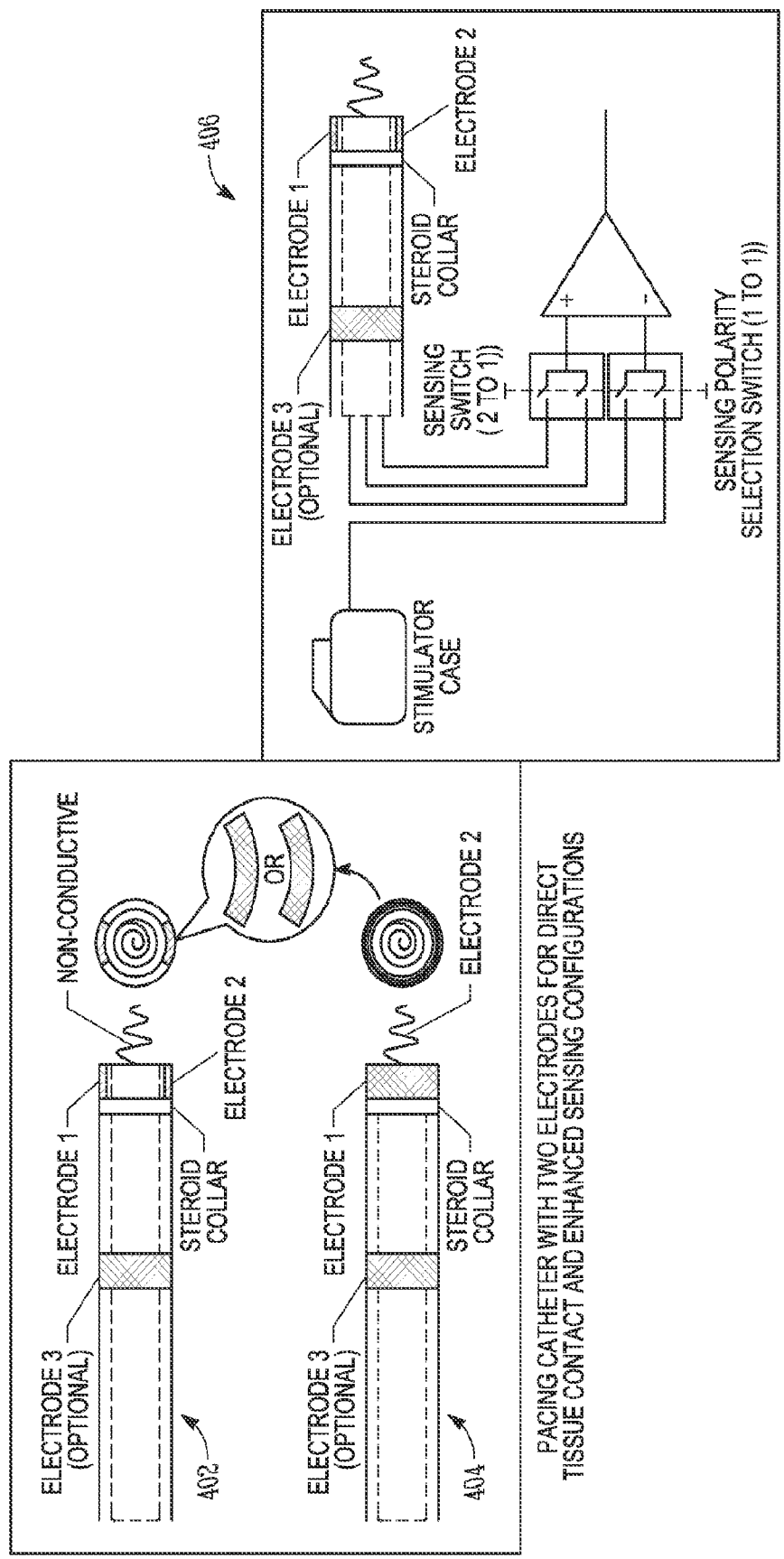
FIG. 8 shows examples of pacing lead configurations, consistent with an embodiment of the present invention.

Aspects of the present subject matter can relate to various pacing lead configurations useful for providing treatment. FIG. 8 shows examples of such pacing lead configurations. The present subject matter is not limited to the configurations shown in FIG. 8. Variations departing from the figures and discussion thereof are therefore envisioned.

The pacing lead 402 of FIG. 8 depicts a particular example of the present subject matter. Pacing lead 402 can be implemented with two or three electrodes and a fixation mechanism. The fixation mechanism is shown as a helix suitable for fixing the pacing lead to heart tissue at the desired pacing location. Other fixation mechanisms are possible. In an example, the fixation mechanism need not be used to provide a pacing signal or reference point and therefore need not be conductive. Electrode 1 and electrode 2 can be located on the distal end of pacing lead 404. In an example, each of electrode 1 and electrode 2 is located at or near the perimeter of the distal tip of the pacing lead. In an example, the electrodes can be implemented concentrically (e.g., different distances from the center of the pacing lead). Each of electrode 1 and electrode 2 can be used to deliver a different component of the pacing signal(s). In an example, each electrode can carry a signal component of opposing polarity from that of the other electrode. The arrangement of the fixation mechanism and electrode placement can be particularly useful for helping ensure that solid contact (e.g., electrical and physical) exists between the heart tissue and the electrodes. This can help facilitate the effective penetration of the pacing components into the heart tissue and thereby the stimulation of the conduction system at or near the His Bundle, such that depolarization occurs primarily using the faster conduction system at or near the His Bundle, rather than via slower cell-to-cell conduction.

Various examples can include a third electrode (e.g., electrode 3). This electrode can provide one or more additional pacing signal components. In an example, the third electrode can provide a reference signal component. Some examples can include different combinations of the electrodes. In an example, electrode 1 and electrode 3 can be used to deliver signal components, while electrode 2 is not used.

Pacing lead 402 is also shown with two different implementations of the contact area of electrode 1 and electrode 2. In a first implementation, the electrodes can be relatively flat. In a second implementation, the electrode 1 and electrode 2 can be implemented with a series of raised portions (indicated by circles). These and other variations of the electrodes can create different effective resistances between the electrodes and the heart tissue. Accordingly, various other variations are possible including, but not limited to, modifications to the effective surface area (e.g., using highly porous electrodes).

Pacing lead 404 depicts another possible implementation consistent with the present subject matter. In this implementation the fixation mechanism can be used as one of the electrodes for delivering pacing components. Assuming the fixation mechanism physically penetrates the heart tissue, the pacing component for electrode 2 can be delivered from within the heart tissue. In an example, substantially all of the fixation mechanism can be conductive. In an example, a select portion of the fixation mechanism can be conductive. For instance, the tip of the fixation mechanism can be conductive, while the portion of the fixation mechanism located proximal to the end of pacing lead 404 can be non-conductive. Such selective location of the conductive portion can help allow for control of the effective spatial/temporal stimulation (e.g., virtual electrode properties) delivered to the heart tissue.

Pacing lead configuration 406 represents another implementation of the present subject matter where one or more of the electrodes can be used to sense one or more electrical signals of the heart. In an example, such as shown, a sensing switch can allow for selectively using the electrodes such as for either delivering pacing components or for sensing electrical signals of the heart. In an example, sensing can be useful for assessing the need for pacing signals. In an example, pacing can be suspended for a period of time. The sensing switch can be modified to allow for sensing of intrinsic heart function. The result of the sensing can be used for a variety of purposes, including determining whether extrinsic pacing should be started or resumed.

The present inventors have also recognized, among other things, that in some patients with intraventricular conduction defects there can be more than two levels of pacing thresholds. Instead of a pacing threshold consistent with the traditional all-or-nothing capture, a continuum of changes in the pacing effectiveness (e.g., QRS morphology) was observed. These changes/improvements were seen as the stimulation amplitude of the pacing (XSTIM) was increased, and continued up to a saturation point.

Without being bound by theory, it is believed that the His bundle may include a large number of diffuse fibers that begin branching quickly within the ventricles. Accordingly, it is believed that increased pacing-signal amplitude/strength can generate a virtual electrode that reaches further into the His bundle (or fibers branching immediately thereafter) to stimulate fibers distal to those fibers accessible at lower pacing-signal amplitudes (e.g., proximal root). Surprisingly, more and more regions of the conduction system are possible to be brought in electrical and mechanical synchrony as the signal amplitude increases. Thus, rather than using an all-or-nothing capture threshold determination, a gradient response can be observed.

Aspects of the present subject matter relate to pacing solutions that take advantage of the gradient responsiveness of near His-bundle pacing. Pacing delivered by one or more electrodes can be characterized such as according to the spatial-temporal relationships of depolarization of cells. A virtual electrode can be understood as spatial-temporal depolarization of cells that is not centered about a physical electrode or other source of electrical stimulus. Thus, the effective location of the stimulus can be other than the physical location of a stimulus source/electrode. It is believed that manipulation of such virtual electrodes (e.g., manipulation of location, size, orientation and/or duration) can be particularly useful.

According to an embodiment of the present subject matter, a pacing therapy can be implemented for treating diseased hearts. The pacing therapy can include modifying the pacing parameters such as using one or more criteria that can recognize or make use of the existence of gradient responsiveness. These pacing parameters can include, but are not limited to, titration of pacing output level (e.g., amperes, voltage, power and/or duration), selection of different pacing waveforms and/or minor modification in pacing location. In an example, the modification of pacing parameters can be implemented to provide different virtual electrodes, whether different in size, location, shape or magnitude.

While certain implementations of the present subject matter can use an XSTIM-type waveform, in an example, the present subject matter need not be restricted to the XSTIM waveform. Various other pacing waveforms can also be possible including, but not limited to, monophasic, biphasic, or multi-phasic waveforms.

The effectiveness or completeness of the capture of His bundle can be determined such as by using one or more different criteria. A few non-limiting examples of criteria can include narrowed QRS width, the degree of fractionation of the QRS in the different leads, the orientation of the QRS vector, and/or one or more mechanical or hemodynamic sensors, (e.g., a right ventricular pressure sensor from which left-sided variables can be extrapolated or inferred).

In an example, a pacing electrode site can be located using a relatively strong pacing signal that can be applied near the His Bundle. In patients with a ventricular conduction defect, this location can be determined in response to one or more criteria indicating whether electrical bypass of a conduction defect has been obtained. After a desired pacing site is located, one or more pacing parameters can be adjusted, such as to determine the optimal pacing parameters. The effects of the pacing parameters can be monitored and compared. One or more gradient response characteristics can be used to determine the desired one or more pacing parameters. Thus, the pacing parameters can be selected using a fine-tuned analysis of one or more gradient response characteristics, rather than an analysis relying upon an all-or-nothing capture of the His Bundle.

The present inventors have also recognized, among other things, that preserved ejection fraction (EF) heart failure (HF) patients can also benefit from atrial pacing, such as at rates higher than the intrinsic sinus node rates. Some preserved EF HF patients suffer from chronotropic incompetence. Restoring the ability of the cardiac rate to increase with an increase responsive to an oxygen demand by the body can help relieve them of symptoms and can be beneficial for their well being.

In an example, a rate responsive pacemaker can be implemented. The pacemaker can be used to restore chronotropic competence to preserved EF HF patients using near His pacing, such as to perform an electrical bypass and improve both systolic and diastolic function at the same rate it restores chronotropic competence to these patients.

In an example, extrinsic pacing can be recurrently halted, such as periodically. During this halted period, the intrinsic properties can be observed and the pacing can be resumed or modified accordingly. A specific, non-limiting, implementation can includes the following:

1) Pacing can be periodically stopped for a period of time (e.g., for a 1 minute). In an example, the periodicity can be implemented every N number of programmable beats or X time period (e.g., every hour or once a day). This setting can be physician programmable and can depend upon the condition of the patient or one or more other factors.

2) During a non-pacing period, the ventricular activation can be sensed (either with no ventricular pacing, or pacing on top of the ventricular sensing). The sensed activation can be used to establish beat-by-beat series of R-to-R times, where R represents the time a ventricular activation is sensed.

3) In an example, sensing can be implemented over a time window (e.g., from 10 ms to 300 ms). During the time window, one or more events other than a detected R can also be sensed and tracked. These events can include other lower level ($\frac{1}{2}$ to $\frac{1}{100}^{th}$ of the amplitude of the R wave) events. An event series (S) can be created or saved, such as for each possible combination of the following parameters: S (time to detection; detection amplitude; fc; fb); where f is the frequency response characteristics, fc is the center frequency, and fb is the bandwidth of the filter used to decrease or eliminate sensing noise and separate the sensed atrial event. At first follow up or after the implant, the complete set of parameters can be tested, such as with the patient at rest, seated, and supine. After the initial follow up, the parameter set can be tested, such as in 1 minute of no-pacing intervals. The parameter set can be modified incrementally (e.g., 1 value up or 1 value down) from the original optimum parameter set found at the first setup for the patient at the initial follow up. This can help obtain convergence in changing conditions to the optimum set. The following parameter set provides an illustrative example of sets of incremental settings:

a. Time to detection: 10-50 ms; 50-100; 100-150; 150-200; 200-250; 250-300 ms b. fc: 5 Hz; 7.5 Hz; 10 Hz; 12.5 Hz; 15 Hz; 17.5 Hz; 20 Hz; 22.5 Hz; 25 Hz; 30 Hz c. fb: 0.5 Hz; 1 Hz; 1.5 Hz; 2 Hz; 2.5 Hz; 3 Hz; 3.5 Hz; 4 Hz; 5 Hz d. Detection amplitude: R/2; R/4; R/8; R/16; R/32; R/64; R/128

4) The processor of the implantable pulse generator (PG) can compare the R to R data series with each of the data series created by the combination of parameters, such as to determine whether one of them provides an adequate cross-correlation (e.g., correlation of 1.0) with the time series of the R to R intervals. The parameters used to optimize this cross-correlation can then be used to program the memory of the device. If the cross-correlation goes below a threshold level (e.g., 0.8), the device can respond appropriately, such as by disabling the atrial tracking mode. Subsequently, a new startup setup can be attempted to improve the cross-correlation beyond the threshold level. This can be implemented by testing whether the patient has a regular intrinsic rhythm before stopping pacing and by verifying ventricular sensing such as at a rate higher than 50 bpm. If an adequate level cannot be reached, the device can use VVI pacing. In an example, a maximum of a specified number (e.g., three) attempts can be implemented before using VVI pacing.

The processor can also find the amplitude that provides the least detections in the optimum window to be used in step (5).

5) The optimum time to detection found in the previous step can be used, such as where the synchronization with the P (or atrial sensed wave) is lost and an R wave (or ventricular detection) is detected at the high detection amplitude setting found at the end of step 4. If that event is detected, then a search for another atrial event can be started using the previous R to R interval. The interval can be incrementally decremented such as from the detected settings found in step 4.

6) The detection window for another P wave can (programmable depending on patient) also be limited to one or more times that are within the previous history of R to R intervals or P to P intervals (with no intervening R sensed event) such as plus and minus a specified number of 1 or more (programmable) standard deviations of those intervals. When switching from sensing to atrial tracking with ventricular pacing, the history of R to R intervals can be used and adjusted (e.g., reduced) relative to the optimum time to detection previously found by the processor. This history can then be adjusted, at the start of pacing to P to P interval equivalents, when no more adjustment for time to detection is required.

Figure 9:
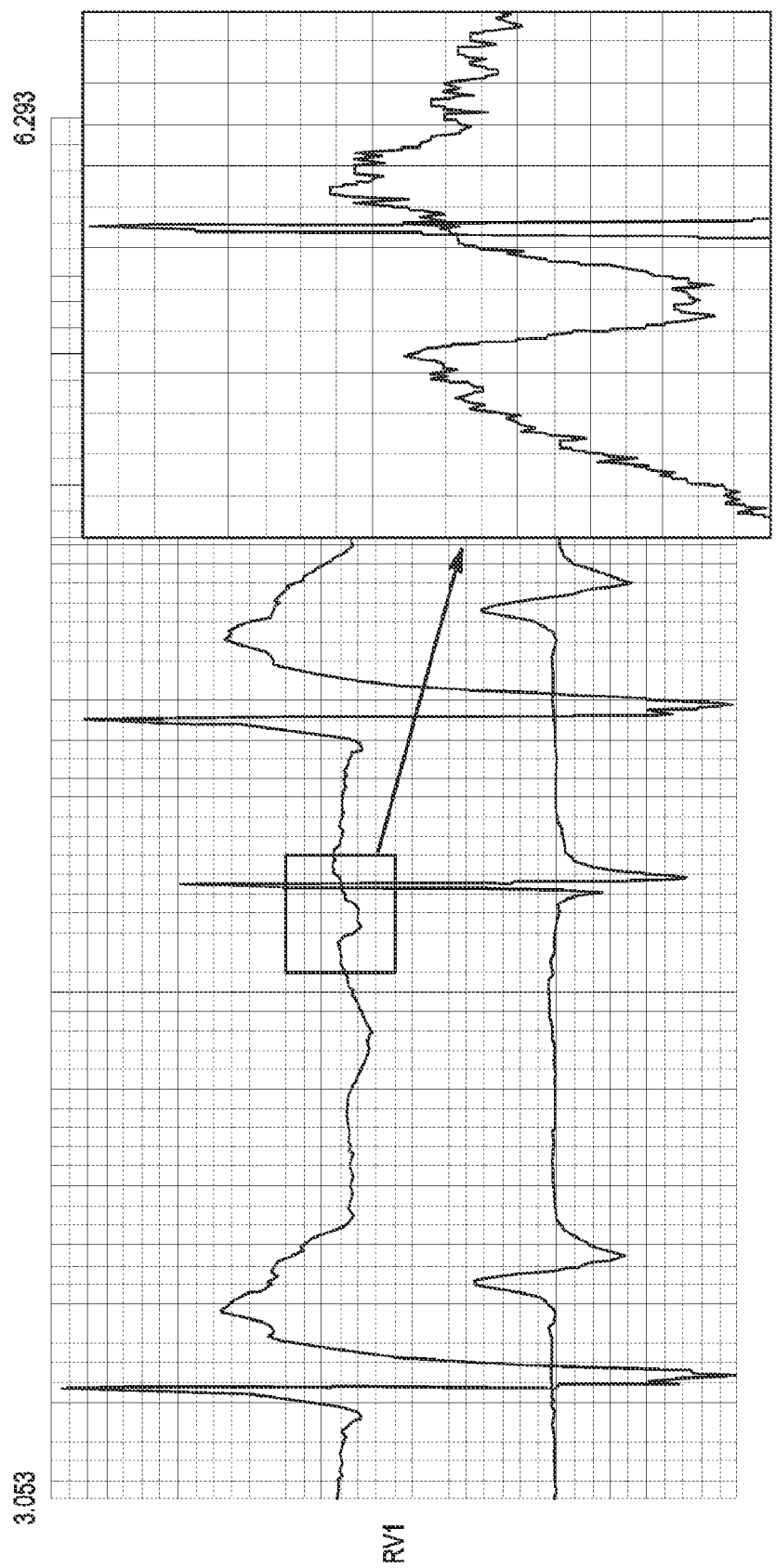
FIG. 9 shows an example of an atrial wave that is sensed using an electrode placed near the His bundle, consistent with an embodiment of the present invention.

A multitude of variations from these steps are possible. These variations can include, but are not limited to, different mechanisms for characterizing R to R intervals, additional and/or different parameter settings, additional pacing profiles or different sensing configurations. FIG. 9 shows an example of an atrial wave that is sensed using an electrode placed near the His bundle.

The present inventors have also recognized that embodiments of the present subject matter can relate to the use of one or more electrophysiological and/or mechanic hemodynamic sensors. These sensors can provide feedback that can allow for the pacing therapy, discussed herein, to be adjusted or optimized, such as with one or more specific goals in mind Examples of one or more criteria that can be considered in developing an optimal pacing solution include, but are not limited to, pacing output amplitude, QRS width, AV delay, pulse pressure, movement of the patient (e.g., accelerometer), change in pressure per time (dP/dt), and/or surrogate end-diastolic pressure from the pulmonary artery/veins.

In an example, the desired location of the electrical stimulus can be determined such as through analysis of the sensor feedback. For instance, the position of the pacing electrode(s) can be determined as a function of the effectiveness of the treatment toward a desired treatment goal.

One example of such a goal is the improvement of dP/dt, such as for patients exhibiting poor dP/dt due to heart failure or other causes. One or more treatment parameters can be automatically selected, for example, as a function of the amount of improvement in dP/dt (minimum and/or maximum) that is sensed for each position. Another goal can be the desired AV delay of the heart. The pacing timing can be adjusted according to the desired AV delay. For instance, the AV delay can be adjusted to help control the preload, while maintaining synchronicity in the heart. The narrowing of the QRS width can be used as yet another factor.

These and/or other goals can be furthered by adjusting one or more components of the pacing. These components can include, but are not limited to, position of one or more pacing electrodes, pacing signal voltage, pacing signal amperage, pacing signal polarity, pacing signal morphology, pacing signal duration, and/or pacing signal timing.

In an example, the pacing location can be determined such as by using relatively high pacing signal strength and using an XSTIM type waveform. Using a strong XSTIM waveform can be particularly useful for facilitation locating the desired position. This position can be determined using feedback from one or more sensors. For instance, the effect of proper capture of the conduction system (e.g., to bypass conduction abnormalities) are not necessarily limited to any one type of feedback. After capture of the conduction system is observed, additional fine tuning of the placement can take place, if so desired. This can include looking for the most improvement in one or more of the feedback signals. Once the position is determined, a desired pacing-signal profile can be determined. This can be accomplished, for example, by iteratively modifying one or more aspects of the pacing profile and assessing the effect on the feedback signal(s). In one such iterative modification, a pacing signal threshold can be determined such as by reducing the pacing signal strength until the improvement is no longer present, or has decreased significantly. This pacing signal threshold can then be used, such as to set the pacing signal at a level that is sufficiently higher than the threshold. In another such iterative modification, a set of different pacing signal polarities, orientations, timings and/or waveform morphology can be used. The desired pacing profile can be selected from the various pacing profiles as a function of the resulting feedback signals.

In an example, pacing can be implemented to treat patients exhibiting heart failure with preserved ejection fraction (EF). In an example, an electrical stimulus can be provided near the His Bundle such as to capture one or more contractions of both ventricles while bypassing conduction defects. In an example, the conduction defects can exhibit one or more characteristics associated with distal or diffuse blocks of the left or right ventricle. In an example, the electrical stimulus can be the XSTIM waveform. In an example, rate responsive pacing for the atrium can be used in conjunction with ventricular pacing through electrical stimulus at or near the His Bundle. The ventricular pacing can thereby follow the intrinsic pacing rate of the heart. This can be particularly useful for providing relatively normal activation of the ventricles with intrinsic pacing rates.

Figure 10:
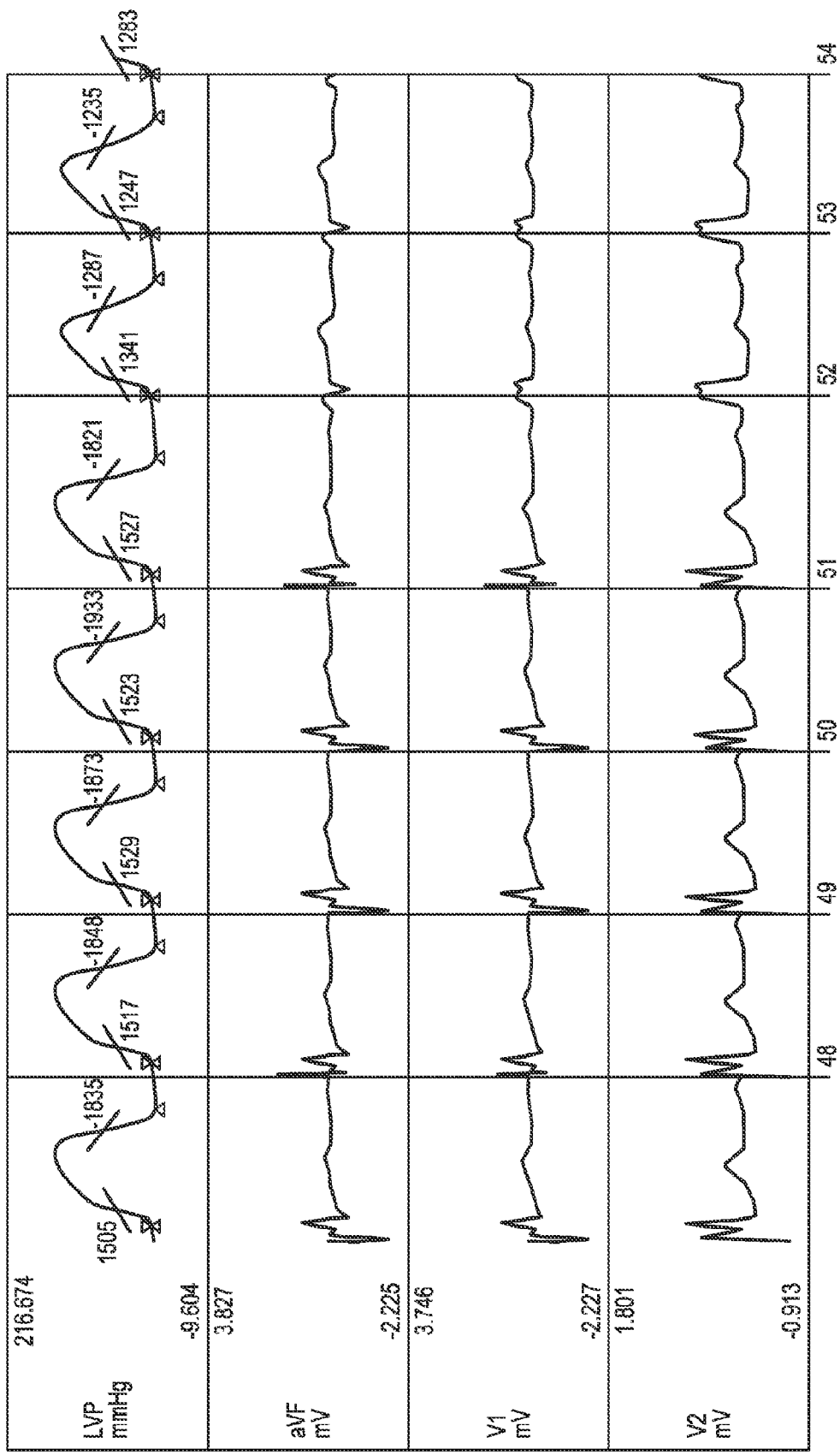
FIG. 10 shows a comparison of intraventricular pressure of the left ventricle for a patient with and without pacing according to the methods discussed herein.

FIG. 10 shows an example of a comparison of intraventricular pressure of the left ventricle for a patient with and without the near His pacing discussed herein. The waveform labeled "LVP" represents the intraventricular pressure of the left ventricle obtained with a Millar catheter. The maximum rate of pressure change in pressure per time unit (dP/dtmax) is shown to be higher in the patients using the present pacing.

Embodiments of the present subject matter have been shown to improve the dP/dtmax in patients. The following data was obtained from two patients and shows improvement in both dP/dtmax and dP/dtmin.

Patient 1
EF=60%; LVEDD=38 mm; QRS width=132 ms
Delta dP/dtmax=16.8%
Delta dP/dtmin=21.6%
Patient 2
EF=60%; LVEDD=38 mm; QRS width=145 ms
Delta dP/dtmax=12.9%
Delta dP/dtmin=7.5%

While the results varied somewhat between the patients, the results suggest that treatment according to the present subject matter can be particularly beneficial for HF patients with a preserved EF.

In an example, pacing from a right-ventricular lead can be used to provide electrical bypass of a conduction abnormality, which can be a distal and/or diffuse ventricular block. This ventricular pacing can be determined using intrinsic heart rate. Using the intrinsic heart rate can be particularly useful for preserving the natural function of the circulatory system in response to patient needs, such as heart rate changes triggered by physiological needs (e.g., increased for physical exertions or decreased during sleep).

In an example, use of intrinsic heart rates can be implemented by monitoring atrial-activation. For instance, intrinsic heart rate monitoring can be implemented by detecting the intrinsic depolarization of the atrium (e.g., P-wave signal). The monitoring can be accomplished using one or more suitable sensors and techniques. As a non-limiting example, the sensing can be implemented using a sensing electrode located in the atrium or ventricle. For instance, a sensing electrode located in the atrium can sense the intrinsic activation of the heart. In another instance, a sensing electrode can be positioned in the (right) ventricle. For example, a pacing electrode properly positioned near the His Bundle can be sufficient to detect atrial depolarization or a signal representative thereof.

Figure 11:
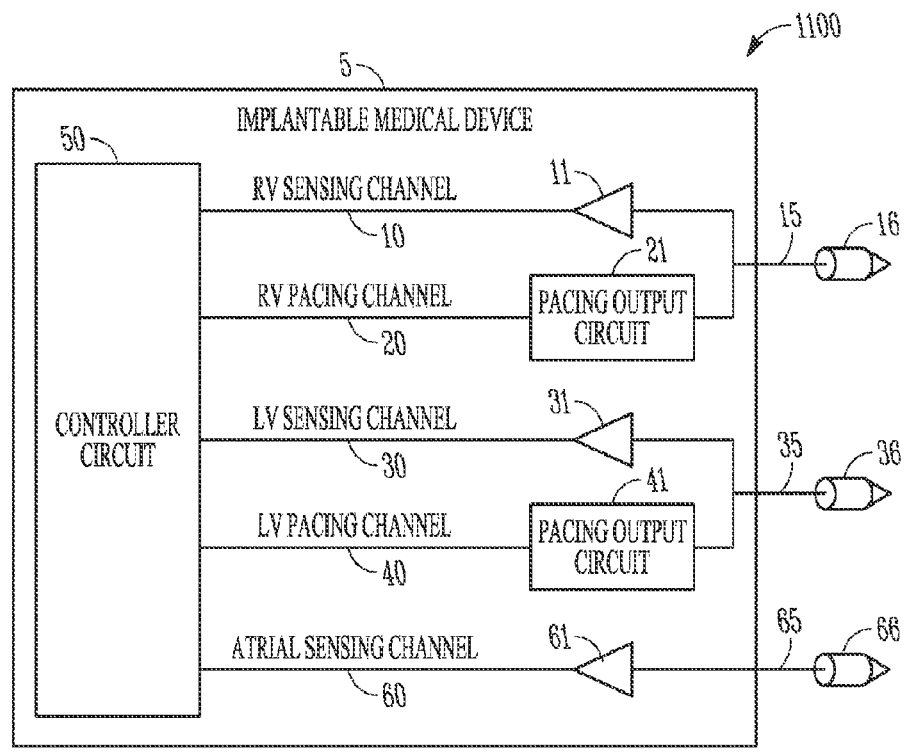
FIG. 11 illustrates generally an example of a system for delivering cardiac therapy.

FIG. 11 illustrates generally an example of a system 1100 for delivering cardiac therapy. In an example, the system 1100 can include an implantable medical device (IMD) 5 (e.g., a pacemaker, a defibrillator, or one or more other cardiac rhythm management devices) having a processor 50, a right ventricular sensing channel 10, a right ventricular pacing channel 20, a left ventricular sensing channel 30, a left ventricular pacing channel 40, and an atrial sensing channel 60. The atrial sensing channel 60 can include at least one of a right atrial sensing channel or a left atrial sensing channel. In certain examples, the system 100 can include an atrial pacing channel. In other examples, the IMD 5 can include a combination of at least one of the a right ventricular sensing channel 10, the right ventricular pacing channel 20, the left ventricular sensing channel 30, the left ventricular pacing channel 40, the atrial sensing channel 60, or the atrial pacing channel.

In the example of FIG. 11, the right ventricular sensing channel 10 includes a sense amplifier 11, the left ventricular sensing channel 30 includes a sense amplifier 31, the right ventricle pacing channel 20 includes a pacing output circuit 21, the left ventricular pacing channel 40 includes a pacing output circuit 41, and the atrial sensing channel 60 includes a sense amplifier 61. In an example, the atrial pacing channel can include a pacing output circuit. In various examples, a single pacing output circuit can be used for one or more of the pacing atrial or ventricular pacing channels. In other examples, the right ventricular sensing channel 10 or the right ventricular pacing channel 20 can be coupled to an electrode 16 disposed on a lead 15 or elsewhere, the left ventricular sensing channel 30 or the left ventricular pacing channels 40 can be coupled to an electrode 36 disposed on a lead 35 or elsewhere, or the atrial sensing channel 60 can be coupled to an electrode 66 disposed on a lead 65 or elsewhere.

In certain examples, the lead 15 can be configured to electrically couple the sense amplifier 11 or the pacing output circuit 21 to the electrode 16, which can be configured to be located in a right ventricle, such as in the septal region, the free wall region, or another region of the right ventricle. Similarly, the lead 35 can be configured to electrically couple the sense amplifier 31 or the pacing output circuit 41 to the electrode 36, which can be configured to be located in, on, or near a left ventricle, such as in the septal region, the free wall region, or another region of the left ventricle or in the coronary vasculature. Further, the lead 65 can be configured to electrically couple the sense amplifier 61 to the electrode 66, which can be configured to be located in at least one of a right atrium or a left atrium of the subject 101.

In the example of FIG. 11, the processor 50 can be an implantable component, an external component, or a combination or permutation of an implantable processor and an external processor. In an example, if at least a portion of the processor 50 includes an external processor, then the processor 50 can be configured to be communicatively coupled (such as via inductive telemetry, RF communication, or one or more other communication protocols) with the remaining implantable components (such as the sense amplifier 11, 31, the pacing output circuit 21, 41, the lead 15, 35, or the electrode 16, 36). In an example, the implantable processor can be configured to have reduced or minimal functionality or power consumption. In certain examples, it can be advantageous for the processor 50 to include an external processor for computing complex operations, such as to classify or otherwise identify a tachycardia rhythm. In other examples, the external processor can include an external device that can be either local or remote. In an example, the processor 50 can include a microcontroller, a microprocessor, a logic circuit, or other processor.

In an example, the pacing output circuit 21 can be configured to generate an electrical energy, such as a ventricular pacing signal, configured to be delivered to one or more electrodes in, on, or near a heart, such as a location near a His bundle of the heart. In certain examples, the one or more electrodes can be coupled to a lead configured to be located in a right ventricle of the heart. In other examples, one or more of the electrodes can be included on a second lead, on the IMD 5, or on one or more other devices at one or more other locations.

In an example, the ventricular pacing signal can include one or more signal component (e.g., the XSTIM waveform, having a positive component and a negative component with respect to a reference component). In an example, the pacing output circuit 21 can include separate terminals for each signal component. The pacing output circuit 21 can include a first terminal configured to deliver a first signal component, a second terminal configured to deliver a second signal component, and a third terminal configured to deliver a third signal component. In an example, the first and second signal components can include components of substantially opposing polarity with respect to a reference component (e.g., the first component can include a positive component, the second component can include a negative component, etc.). In an example, the third signal component can include the reference component.

In an example, the lead 15 can include a pacing lead configured to deliver one or more electrodes to a location near the His bundle in the right ventricle of the heart. In an example, the first, second, and third terminals can be configured to deliver the XSTIM waveform. The XSTIM waveform can include an overlapping biphasic stimulation pulse with respect to a reference (e.g., ground), where the first and second signal components (e.g., pulses) at least partially overlap in time. In an example, the first signal component can have the same magnitude (but opposite polarity) and duration of the second signal component, and can completely overlap in time. In other examples, the first signal component can have a duration longer or shorter than the second signal component, a magnitude greater or less than the second signs component, or the first signal component can lead or follow the second signal component in time.

In an example, the lead 15 can be configured to deliver a first, second, and third electrode to a location near the His bundle, and to deliver the first, second, and third signal components to the first, second, and third electrodes, respectively. In other examples, the lead 15 can include at least one of the first, second, and third electrodes, and one or more other leads, or the IMD 5, can include one or more of the remaining electrodes.

In an example, the sense amplifier 11 can include a cardiac function sensor configured to provide information used to control reversing polarity of the first and second signal components. In an example, the sense amplifier 11 can be coupled to the pacing output circuit 21.

In an example, the sense amplifier 61 can include an atrial sensing circuit configured to sense atrial heart contractions, and the processor 50 can include a controller circuit configured to determine a paced AV delay, and to time the paced AV delay from a sensed atrial heart contraction. The controller circuit can include a temporary mode in which the paced AV delay is set to a value that is specified to provide a reduced cardiac output relative to a cardiac output at maximum dP/dt while the pacing output circuit 21 provides the ventricular pacing signal to deliver to an electrode near the His bundle in a right ventricle of a heart to pace the right and left ventricles and improve synchronization of at least one of the ventricles relative to intrinsic activity. In an example, the paced AV delay can be set to a value that allows mitral valve closure before completion of a left atrial contraction.

In an example, the sense amplifier 61 can include an atrial heart contraction sensing circuit, the sense amplifier 11 can include a ventricular heart contraction sensing circuit, and the processor 50 can include a controller circuit coupled to the atrial heart contraction sensing circuit, the ventricular heart contraction sensing circuit, and the pacing output circuit 21, the controller circuit comprising an atrial tracking mode for controlling the pacing output circuit to deliver paces in response to sensed atrial heart contractions, and wherein the controller circuit is configured to inhibit pacing to sense an underlying ventricular heart rhythm, and to exit the atrial tracking mode when the controller determines that the underlying ventricular heart rhythm is not well correlated to a ventricular heart rhythm obtained during the atrial tracking mode when pacing is enabled.

Figure 12:
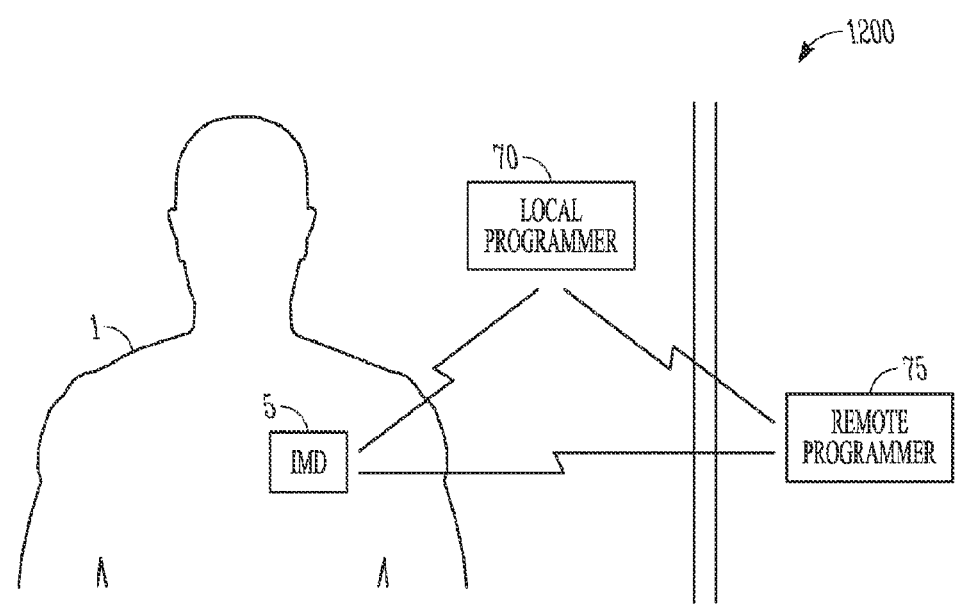
FIG. 12 illustrates generally an example of a portion of a system including an IMD configured to be implanted in a subject.

FIG. 12 illustrates generally an example of a portion of a system 1200 including an IMD 5 configured to be implanted in a subject 101. The system 200 can include at least one of a local programmer 70 or a remote programmer 75. Both the local programmer 70 and the remote programmer 75 are external components. In an example, the local programmer 70 can include a hand-held programmer or other programmer capable of being positioned in communication proximity to the processor 50. The proximity range between the processor 50 and the local programmer 70 can vary depending upon the type of data communication and is bound by the physical constraints of the communication type. In an example, the remote programmer 75 can include any programmer configured to communicate with the IMD 5 either directly or indirectly, such as through another device (e.g., a router, the local programmer 70, etc.). In various examples, the remote programmer 75 can be configured to communicate with or store information from a plurality of implanted or external devices, and the remote programmer 75 can be configured to be located a long distance from the subject 1.

In an example, the local programmer 70 or the remote programmer 75 can be configured to send information to or receive information from the IMD 5. The information can include programming information, subject data, device data, or other instructions, alerts, or other information. Further, the local programmer 70 or the remote programmer 75 can be configured to communicate the sent or received information to a user or physician, such as by sending an alert via email of the status of the subject 1 or the system components.

The skilled artisan will recognize that the various aspects discussed in connection with the present invention can be implemented in a variety of combinations and manners. Moreover, aspects discussed in connection with the various references disclosed and incorporated herein can be used in combination with aspects of the present invention. To the extent that the references indicated herein include a number of similar figures and related discussions, the skilled artisan would appreciate the interoperability of aspects disclosed therein even for figures not common between documents. The teachings throughout these documents relate to aspects that can be used in combination with embodiments of the present invention. Accordingly, the documents are incorporated by reference in their entirety. For instance, the following patent documents contain descriptions and figures depicting various pacing electrodes and associated circuitry, and such embodiment(s) can be used in combination with aspects of the present invention: U.S. patent application Ser. No. 12/147,293 to Qingsheng Zhu et al., and filed Jun. 26, 2008, now U.S. Pat. No. 8,014,861, U.S. Provisional Patent Applications concurrently filed on Jun. 29, 2007, now expired, to Qingsheng Zhu and identified by the following Ser. Nos. 60/947,308 (Endocardial Pacing For Resynchronization), 60/947,310 (Directable Sheath Arrangement For Ventricular Resynchronization), 60/947,322 (System And Method For Ventricular Pacing With Monitoring And Responsiveness To Pacing Effectiveness), 60/947,327 (Electrical Circuit Arrangement And Method For Pulse Control Of Endocardial Pacing For Resynchronization), 60/947,336 (Endocardial Pacing For Resynchronization And Defibrillator), 60/947,342 (Endocardial Pacing For Resynchronization And Treatment Of Conduction Abnormalities), U.S. Provisional Patent Application identified by Ser. No. 61/020,511 (A Cardiac Stimulation Catheter With Two Contacting Electrodes To The Cardiac Tissue And Its Connections To The Stimulator) filed on Jan. 11, 2008 to Qingsheng Zhu et al., and U.S. patent application Ser. No. 11/300,611 (Ventricular Pacing) filed Dec. 13, 2005, now U.S. Pat. No. 7,512,440, to Daniel Felipe Ortega et al. and U.S. patent application Ser. No. 11/300,242 (Pacemaker Which Reestablishes Or Keeps The Physiological Electric Conduction Of The Heart And A Method Of Application) filed Dec. 13, 2005, now U.S. Pat. No. 8,346,358, to Daniel Felipe Ortega et al. and Argentine Patent Application Ser. No. 20040104782 (A New Pacemaker Which Reestablishes Or Keeps The Physiological Electric Conduction Of The Heart And A Method Of Application) filed Dec. 20, 2004, to Daniel Felipe Ortega et al. Each of these patents documents is incorporated by reference in their entirety.

This application incorporates by reference: U.S. patent application Ser. No. 11/300,611, now U.S. Pat. No. 7,512,440, International Patent Application PCT/US2005/045044, Argentina Patent Application 2004/0104782, U.S. patent application Ser. No. 11/300,242, now U.S. Pat. No. 8,346,358, U.S. patent application Ser. No. 12/147,293, now U.S. Pat. No. 8,014,861, Patent Application Ser. No. 60/947,308, International Patent Application PCT/US2008/068618, U.S. patent application Ser. No. 12/147,317, now U.S. Pat. No. 8,326,423, U.S. Patent Application Ser. No. 60/947,310, International Patent Application PCT/US2008/068627, U.S. patent application Ser. No. 12/147,339, now U.S. Pat. No. 8,010,191, U.S. Patent Application Ser. No. 60/947,322, International Patent Application PCT/US2008/068630, U.S. patent application Ser. No. 12/147,356, now U.S. Pat. No. 8,050,756, U.S. Patent Application Ser. No. 60/947,327, International Patent Application PCT/US2008/068632, U.S. patent application Ser. No. 12/147,425, now U.S. Pat. No. 8,005,544, U.S. Patent Application Ser. No. 60/947,336, International Patent Application PCT/US2008/068635, U.S. patent application Ser. No. 12/147,369, now U.S. Pat. No. 8,010,192, U.S. Patent Application Ser. No. 60/947,342, International Patent Application PCT/US2008/068654, U.S. patent application Ser. No. 12/147,376, now U.S. Pat. No. 8,423,139, U.S. Patent Application Ser. No. 61/020,511, International Patent Application PCT/US2008/068647, U.S. patent application Ser. No. 12/249,508, now U.S. Pat. No. 8,290,586, International Patent Application PCT/US2009/060293, all of which are commonly assigned to Action Medical, Inc., all of which are respectively incorporated herein by reference in their respective entireties.

The various embodiments described above are provided by way of illustration only and should not be construed to limit the invention. Based on the above discussion and illustrations, those skilled in the art will readily recognize that various modifications and changes may be made without strictly following the exemplary embodiments and applications illustrated and described herein. Such modifications and changes do not depart from the scope of the present invention.

The claimed invention is:

1. An apparatus comprising:
   a pacing output circuit configured to generate a ventricular pacing signal to deliver to an electrode near the His bundle in a right ventricle of a heart to pace the right and left ventricles and improve synchronization of at least one of the ventricles relative to intrinsic activity, the pacing output circuit comprising:
   a first terminal, configured to deliver a first signal component;
   a second terminal, configured to deliver a second signal component;
   a third terminal, configured to deliver a reference signal component; and
   wherein the first and second signal components are provided in opposite polarity from each other with respect to the reference signal component,
   wherein the pacing output circuit is configured to recurrently reverse polarity of the first and second signal components from a first polarity arrangement to a second polarity arrangement,
   wherein the polarity of the first and second signal components is reversed from the first polarity arrangement to the second polarity arrangement after N beats or time corresponding to the N beats,
   wherein the polarity of the first and second signal components is reversed again from the second polarity arrangement to the first polarity arrangement after M beats or time corresponding to the M beats, and wherein N is greater than M.

2. The apparatus of claim 1, further comprising a pacing lead configured to deliver an electrode near the His bundle in a right ventricle of a heart.

3. The apparatus of claim 1, wherein the pacing output circuit is configured to provide the opposite polarity first and second signal components at least partially overlapping in time.

4. The apparatus of claim 1, comprising a cardiac function sensor configured to provide information used to control reversing polarity of the first and second signal components by the pacing output circuit.

5. The apparatus of claim 1, comprising:
   an atrial sensing circuit, configured to sense atrial heart contractions;
   a controller circuit, configured to determine a paced AV delay, and to time the paced AV delay from an atrial heart contraction, wherein the controller includes a temporary mode in which the paced AV delay is set to a value that is specified to provide a reduced cardiac output relative to a maximum cardiac output while the pacing output circuit provides the ventricular pacing signal to deliver to an electrode near the His bundle in a right ventricle of a heart to pace the right and left ventricles and improve synchronization of at least one of the ventricles relative to intrinsic activity.

6. The apparatus of claim 5, wherein the paced AV delay is set to a value that allows mitral valve closure before completion of a left atrial contraction.

7. The apparatus of claim 6, wherein the paced AV delay is increased after a period of time specified to allow for the heart to recover at the reduced cardiac output.

8. The apparatus of claim 1, in combination with a guide catheter configured for pace-mapping in a right ventricle at or near the His bundle.

9. The apparatus of claim 1 comprising:
   a ventricular heart contraction sensing circuit; and
   a controller circuit, coupled to the ventricular heart contraction sensing circuit, configured to use information from the ventricular heart contraction sensing circuit to detect a tachyarrhythmia and, in response to the detected tachyarrhythmia, to control the pacing output circuit to deliver the ventricular pacing signal as an anti-tachyarrhythmnia pacing (ATP) pulse to an electrode near the His bundle in a right ventricle of a heart.

10. The apparatus of claim 9, comprising:
    a defibrillation shock circuit, coupled to the controller circuit; and
    wherein the controller circuit is configured to deliver a defibrillation shock when a plurality of the ATP pulses do not restore the tachyarrhythmia to a non-tachyarrhythmia heart rhythm.

11. The apparatus of claim 10, wherein the controller circuit is configured for controlling the pacing output circuit for:
    using at least a first electrode in a right ventricle of the heart for delivering energy relative to a reference electrode;
    generating a pacing signal, responsive to depolarization of an atrium of the heart, including a first signal component and a second signal component having opposite polarity; and
    transmitting, at a pacing rate sufficient for anti-tachycardia pacing (ATP), said first signal component and said second component to said at least a first electrode and, in response thereto, capturing a contraction of a left ventricle of the heart where the contraction is a more rapid and uniform activation than an right ventricular apex ATP pulse.

12. The apparatus of claim, 1, comprising:
    a cardiac function monitor; and
    a controller circuit, coupled to the cardiac function monitor and the pacing output circuit, wherein the controller circuit is configured to determine a desired pacing parameter at least in part by iteratively modifying at least one pacing parameter of the pacing output circuit using information received from the cardiac function monitor.

13. The apparatus of claim 1, comprising:
    a cardiac function monitor; and
    a controller circuit, coupled to the cardiac function monitor and the pacing output circuit, wherein the controller circuit is configured to determine a desired pacing parameter at least in part using information received from the cardiac function monitor regarding at least one of a pacing output amplitude, a QRS width, an AV delay, a pulse pressure, a movement of the patient, a change in blood pressure per time (dP/dt), intraventricular pressure, or a surrogate end-diastolic pressure from a pulmonary artery or vein during pacing of the heart.

14. The apparatus of claim 12, wherein the controller circuit is configured to determine the desired pacing parameter at least in part using gradient capture responsiveness information received from the cardiac function monitor.

15. A method comprising:
generating a ventricular pacing signal to deliver to an electrode near the His bundle in a right ventricle of a heart to pace the right and left ventricles and improve synchronization of at least one of the ventricles relative to intrinsic activity, wherein the pacing signal comprises a first component and a second component of opposite polarity from the first component with respect to a reference signal;
recurrently reversing the polarity of the first and second signal components from a first polarity arrangement to a second polarity arrangement, wherein the recurrently reversing the polarity includes reversing from the first polarity arrangement to the second polarity arrangement after N beats or time corresponding to the N beats, reversing again from the second polarity arrangement to the first polarity arrangement after M beats or time corresponding to the M beats, wherein N and greater than M, and N includes two or more beats.

16. The method of claim 15, further comprising:
determining a paced AV delay, wherein the paced AV delay is timed from an atrial heart contraction, and wherein the paced AV delay is reduced to provide a reduced cardiac output relative to a maximum cardiac output while the pacing signal delivers the ventricular pacing signal to deliver to an electrode near the His bundle in a right ventricle of a heart to pace the right and left ventricles and improve synchronization of at least one of the ventricles relative to intrinsic activity.

17. The method of claim 16, wherein the paced AV delay is increased after a period of time specified to allow for the heart to recover at the reduced cardiac output.

18. The method of claim 16, further comprising increasing the paced AV delay after a period of time specified to allow for the heart to recover at the reduced cardiac output.

* * * * *

UNITED STATES PATENT AND TRADEMARK OFFICE
CERTIFICATE OF CORRECTION

PATENT NO. : 8,688,234 B2
APPLICATION NO. : 13/139951
DATED : April 1, 2014
INVENTOR(S) : Zhu et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Eleventh Day of August, 2015

Michelle K. Lee
*Director of the United States Patent and Trademark Office*